US009662380B2

(12) United States Patent
Jayappa et al.

(10) Patent No.: US 9,662,380 B2
(45) Date of Patent: *May 30, 2017

(54) ***C. PERFRINGENS* ALPHA TOXOID VACCINE**

(71) Applicant: Intervet Inc., Madison, NJ (US)

(72) Inventors: Huchappa Jayappa, Omaha, NE (US); Kevin O'Connell, Omaha, NE (US)

(73) Assignee: Intervet Inc., Madison, NJ (US)

( * ) Notice: Subject to any disclaimer, the term of this patent is extended or adjusted under 35 U.S.C. 154(b) by 183 days.

This patent is subject to a terminal disclaimer.

(21) Appl. No.: 14/608,577

(22) Filed: Jan. 29, 2015

(65) Prior Publication Data

US 2015/0140033 A1    May 21, 2015

Related U.S. Application Data

(63) Continuation of application No. 11/405,198, filed on Apr. 17, 2006, now Pat. No. 8,980,283.

(60) Provisional application No. 60/672,289, filed on Apr. 18, 2005.

(51) Int. Cl.

| | | |
|---|---|---|
| *A61K 39/08* | (2006.01) |
| *A61K 39/02* | (2006.01) |
| *A61K 39/00* | (2006.01) |
| *A61K 39/38* | (2006.01) |
| *A61K 39/40* | (2006.01) |
| *A61K 45/00* | (2006.01) |
| *A61K 47/00* | (2006.01) |
| *A61K 39/108* | (2006.01) |

(52) U.S. Cl.
CPC .......... *A61K 39/08* (2013.01); *A61K 39/0258* (2013.01); *A61K 2039/55* (2013.01); *A61K 2039/552* (2013.01); *A61K 2039/70* (2013.01)

(58) Field of Classification Search
CPC .............. A61K 39/08; A61K 2039/55; A61K 2039/552; A61K 39/0258; A61K 2039/70
See application file for complete search history.

(56) References Cited

U.S. PATENT DOCUMENTS

| | | | |
|---|---|---|---|
| 3,993,636 A | 11/1976 | Maubois et al. | |
| 4,292,307 A | 9/1981 | Zemlyakova | |
| 5,817,317 A | 10/1998 | Titball et al. | |
| 5,851,827 A | 12/1998 | Titball et al. | |
| 6,048,535 A | 4/2000 | Sharma | |
| 6,083,512 A | 7/2000 | Roberts | |
| 8,980,283 B2 * | 3/2015 | Jayappa .................. | A61K 39/08 424/167.1 |
| 2004/0018215 A1 | 1/2004 | Ellison | |
| 2010/0062025 A1 | 3/2010 | Witvliet et al. | |

FOREIGN PATENT DOCUMENTS

| | | |
|---|---|---|
| WO | 93/23543 A1 | 11/1993 |
| WO | 2005/002509 A2 | 1/2005 |
| WO | 2005/016383 A1 | 2/2005 |
| WO | 2006/041933 A2 | 4/2006 |

OTHER PUBLICATIONS

Aucouturier, et al.; "Montanide ISA 720 and 51: a new generation of water in oil emulsions as adjuvants for human vaccines", Expert Rev Vaccines, Jun. 2002; 1(1):111-8.
Ball, et al.; "Purification and characterization of alpha-toxin produced by Clostridium novyi type A", Infect Immun., Jul. 1993; 61(7):2912-8.
Ballard, et al.; "The primary structure of Clostridium septicum alpha-toxin exhibits similarity with that of Aeromonas hydrophila aerolysin", Infect Immun., Jan. 1995; 63(1):340-4.
Batty; "Toxin-Antitoxin Assay"; Methods in Microbiology, Chapter 8, vol. 5A; Edited by J.R. Norris and D.W. Ribbons, (1971), pp. 256-280.
Blatt, et al.; "Protein Solutions: Concentration by a Rapid Method", Science, 1995; 150:224-26.
Boersma, et al.; Res. Immunology, 1992; 143(5):503-12.
Bueschel, et al.; "Prevalence of cpb2, encoding beta2 toxin, in Clostridium perfringens field isolates: correlation of genotype with phenotype", Vet Microbiol., Jul. 1, 2003; 94(2):121-9.
Crouch et al., "Safety and efficacy of a maternal vaccine for the passive protection of broiler chicks against necrotic enteritis", Avian Pathology, Dec. 2010; 39(6):489-97.
Daube, et al.; "Hybridization of 2,659 Clostridium perfringens isolates with gene probes for seven toxins (alpha, beta, epsilon, iota, theta, mu, and enterotoxin) and for sialidase", Am J Vet Res., Apr. 1996; 57(4):496-501.
Engstrom, et al.; "Molecular typing of isolates of Clostridium perfringens from healthy and diseased poultry", Vet Microbiol., Jul. 17, 2003; 94(3):225-35.
EU Pharmacopoeia 5.0:01/2005:0088, pp. 803-804.
Garmory, et al.; "Occurrence of Clostridium perfringens beta2-toxin amongst animals, determined using genotyping and subtyping PCR assays", Epidemiol Infect., Feb. 2000; 124(1):61-7.
Gibert, et al.; "Beta2 toxin, a novel toxin produced by Clostridium perfringens", Gene, Dec. 5, 1997; 203(1):65-73.
Granato, et al.; "Purification and Characterization of the L. Component of *Streptococcus zymogenes* Lysin", Journal of Bacteriology, 1971; 108(2):804-8.
Greenspan, et al.; Nature Biotechnology, 1999, 17:936-37.
Hatheway; "Toxigenic Clostridia", Clinical Microbiology Reviews, Jan. 1990; 3(1):66-98.
Havard, et al.; "Comparison of the nucleotide sequence and development of a PCR test for the epsilon toxin gene of Clostridium perfringens type B and type D.", FEMS Microbiol Lett., Oct. 1, 1992; 76(1-2):77-81.
Heier, et al.; "A field study of naturally occurring specific antibodies against Clostridium perfringens alpha toxin in Norwegian broiler flocks", Avian Dis., Jul.-Sep. 2001; 45(3):724-32.
Herholz, et al.; "Prevalence of beta2-toxigenic Clostridium perfringens in horses with intestinal disoreders", J Clin Microbiol., Feb. 1999; 37(2):358-61.

(Continued)

*Primary Examiner* — Gary Nickol
*Assistant Examiner* — Lakia Tongue

(57) ABSTRACT

The present invention describes vaccines that comprise *C. perfringens* Type alpha toxoids, antigenic fragments thereof, inactivated antigenic fragments of *C. perfringens* Type alpha (Continued)

toxins, or any combination thereof. The present invention further describes methods of using with these vaccines to protect animals against clostridial diseases. The present invention also describes methods of making these vaccines.

18 Claims, No Drawings

(56) References Cited

OTHER PUBLICATIONS

Immerseel, et al.; "Rethinking our understanding of the pathogenesis of necrotic enteritis in chickens", Cell Press, 2008, 17(1):32-36.
Ito, et al.; Japan J. Med. Sci. Biol., 1970; 23:111-15.
Ito, Akiharu; "Alpha toxoid of Clostridium Perfringens. I. Purification and Toxoiding of Alpha Toxin of C. Perfringens", Japan. J. Med. Sci. Biol., 1968; 21:379-91.
Jansen, et al.; Vaccine, Jan. 2005; 23:1053-60.
Justin, et al.; "The first strain of Clostridium perfringens isolated from an avian source has an alpha-toxin with divergent structural and kinetic properties", Biochemistry, May 21, 2002; 41(2):6253-62.
Kulkarini, et al.; "Immunization of Broiler Chickens against Clostridium perfringens-Induced Necrotic Enteritis"; Clinical and Vaccine Immunology; Sep. 2007; 14(9):1070-77.
Lovland, et al.; "Maternal vaccination against subclinical necrotic enteritis in broilers", Avian Pathol., Feb. 2004; 33 (1):83-92.
Lovland et al.; "Severely impaired production performance in broiler flocks with high incidence of Clostridium perfringens-associated hepatitis", Avian Pathology, 2001; 30:73-81.
Manteca, et al.; "A role for the Clostridium perfringens beta2 toxin in bovine enterotoxaemia?", Vet Microbiol., May 1, 2002; 86(3):191-202.
Mietzner, et al.; "A conjugated synthetic peptide corresponding to the c-terminal region of Clostridium perfringens type A enterotoxin elicits an enterotoxin-neutralizing antibody response in mice", Infection and Immunity, 1992; 60 (9):3947-3951.
Miyamoto, et al.; "Complete sequencing and diversity analysis of the enterotoxin-encoding plasmids in Clostridium perfringens type A non-food-borne human gastrointestinal disease isolates". J Bacteriol, Feb. 2006; 188(4):1585-98.
Nagahama, et al.; "Site-directed mutagenesis of histidine residues in Clostridium perfringens alpha-toxin", J. Bacteriol, Mar. 1995; 177(5):1179-85.
Niilo, L.; "Enterotoxigenic Clostridium perfringens type A isolated from intestinal contents of cattle, sheep and chickens", Can J Cop Med. Jul. 1978; 42(3):357-63.
Niilo, L.; "Response of ligated intestinal loops in chickens to the enterotoxin of Clostridium perfringens", Appl Microbiol. Nov. 1974; 28(5):889-91.
Perelle, et al.; "Characterization of Clostridium perfringens Iota-toxin genes and expression in *Escherichia coli*", Infect Immun, Dec. 1993; 61(12):5147-5156.
Rais-Beghdadi, et al.; Applied Biochemistry and Biotechnology, 1998; 74:95-103.
Saint-Joanis, et al.; "Gene cloning shows the alpha-toxin of Clostridium perfringens to contain both sphingomyelinase and lecithinase activities", Mol Gen Genet., Nov. 1989; 219(3):453-60.
Schoepe, et al.; "Naturally occurring Clostridium perfringens nontoxic alpha-toxin variant as a potential vaccine candidate against alpha-toxin-associated diseases"; Infect Immun., Nov. 2001; 69(11):7194-6.
Schoepe, et al.; "Immunization with an alphatoxin variant 121A/91-R212H protects mice against Clostridium perfringens alphatoxin"; Anaerobe, Feb. 2006; 12(1):44-8.
Schotte, et al.; "Significance of beta 2-toxigenic clostridium perfringens infections in aniamls and their predisposing factors—a review"; J Vet Med B [Infect Dis Vet Public Health], Dec. 2004; 51(10):423-6.
Shimizu, et al.; "Complete genome sequence of Clostridium perfringens, an anaerobic flesh-eater"; Proc Natl Acad Sci USA, Jan. 22, 2002; 99(2):996-1001.
Smith, et al.; "Maternally induced protection of young lambs against the epsilon toxin of Clostridium perfrigens using nonactivated vaccine", Am J Vet Res, Jan. 1959; 20:91-3.
Smith, et al.; The Pathogenic Anaerobic Bacteria, (3rd Ed.), Charles Thomas Publishers, 1984, pp. 116.
Songer, J. Glenn; "Clostridial enteric diseases of domestic animals", Clin Microbiol Rev., Apr. 1996; 9(2):216-34.
Stevens, et al.; "Immunization with the C-Domain of alpha-Toxin prevents lethal infection, localizes tissue injury, and promotes host response to challenge with Clostridium perfringens"; J Infect Dis., Aug. 15, 2004; 190(4):767-73.
Steinporsdottir, et al.; FEMS Microbiol Lett., Aug. 1, 1995; 130(2-3):273-8.
Scientific Discussion from EMEA, 2009, found at http://www.ema.europa.eu/docs/en_GB/document_library/EPAR_-_Scientific_Discussion/veterinary/000134/WC500066324.pdf and accessed on Jun. 26, 2013.
Tsutsui, et al.; "Phylogenetic analysis of phospholipase C genes from Clostridium perfringens types A to E and Clostridium novyi"; J Bacteriol., Dec. 1995; 177(24):7164-70.
Van Reis, et al.; Current Opinion in Biotechnology, 2001; 12:208-211.
Von Eichel-Streiber, et al.; "Comparative sequence analysis of the Clostridium difficile toxins A and B"; Mol. Gen. Genet., 1992; 233-260-268.
Wages, et al.; "Necrotic Enteritis", In: Disease of Poultry, 11th ed., (eds., Saif et al.), Iowa State Press, Ames, IA (2003), pp. 781-785.
Wren, et al.; "Nucleotide sequence of clostridium difficile toxin A gene fragment and detection of toxigenic strains by polymerase chain reaction", FEMS Microbiol Lett., Feb. 10, 1990; 70:1-6.
International Search Report for International Application No. PCT/US2006/014669, mailed Sep. 11, 2006—5 pages.

\* cited by examiner

C. PERFRINGENS ALPHA TOXOID VACCINE

CROSS-REFERENCE TO RELATED APPLICATIONS

This application is a Continuation application of U.S. application Ser. No. 11/405,198, filed on Apr. 17, 2006, now U.S. Pat. No. 8,980,283 B2, that claims priority under 35 U.S.C. §119(e) of provisional application U.S. Ser. No. 60/672,289 filed Apr. 18, 2005, the contents of which are hereby incorporated by reference in their entireties.

FIELD OF THE INVENTION

The present invention relates to vaccines comprising C. perfringens Type alpha toxoids, antigenic fragments thereof, inactivated antigenic fragments of alpha toxins, and any combinations thereof. The present invention further relates to methods of using with these vaccines to protect animals against clostridial diseases. The present invention also relates to methods of making these vaccines.

BACKGROUND

Clostridium perfringens (C. perfringens) is an anaerobic bacterium that is naturally found in soil, decaying organic matter, and as part of the normal gut flora of animals, including humans. C. perfringens is also the etiological agent for numerous clostridial diseases found in economically valuable domestic animals. C. perfringens produces a number of toxins that cause pathogenic effects in animals, including the alpha toxin, the beta toxin, the beta 2 toxin, the epsilon toxin, the theta toxin, the mu toxin, the delta toxin, the iota toxin, the kappa toxin, and the lambda toxin. Moreover, C. perfringens encodes other biologically active substances that can cause pathological effects, including: hyaluronidase, acid phosphatase, protease, collagenase, sulfatase and neuraminidase.

Different strains of C. perfringens are designated as biotypes A through E, depending on the spectrum of toxins that the particular bacterium produces [Justin et al., Biochemistry 41:6253-6262 (2002); McDonel, PHARMACOLOGY OF BACTERIAL TOXINS; F Dorner and J Drews (eds.) Pergamon Press, Oxford (1986)]. Initially, such typing was based on serologic neutralization assays in mice or guinea pigs. More recently, molecular typing methods employ polymerase chain reaction (PCR) targeted to genetic sequences that encode one of the numerous toxins of C. perfringens.

Intestinal clostridiosis in horses has been correlated with high concentrations of C. perfringens Type A in the gut. Afflicted equine have a profuse watery diarrhea and a high mortality rate. C. perfringens Type A also has been linked to enteric disease in suckling and feeder pigs, with the symptoms including mild necrotizing enteritis and villous atrophy [Songer, Clin. Micro. Rev, 9(2):216-234 (1996)].

Clostridial diseases caused by C. perfringens are characterized by sudden death in well-fleshed birds with confluent fibrinonecrotic lesions ("Turkish towel") in the small intestine (enteric forms), and/or C. perfringens-associated hepatitis with cholangiohepatitis, or fibrinoid necrosis in the liver. Afflicted birds undergo a rapid course of depression, diarrhea, and dehydration. Mortality ranges from 2% to 50%. Liver pathology leads to carcass condemnations at slaughter.

Necrotic enteritis (NE) is an example of a clostridial enteric disease caused by C. perfringens that leads to significant economic consequences in poultry. The disease is especially common in floor-reared broiler chickens from 2 to 10 weeks of age, though the disease also has been reported in turkeys and caged laying hens. Necrotic enteritis generally occurs in poultry either as a secondary disease, or in a situation in which the normal intestinal microflora are altered so as to allow the abnormal proliferation of pathogenic C. perfringens. The prevalence of subclinical necrotic enteritis is unknown, since the lesions can only be observed through post-mortem examination. However, reports of impaired feed conversion and reduced body weights have been attributed to the subclinical disease [Lovland and Kadhusdal, Avian Path. 30:73-81 (2001)]. Predisposing factors that lead to necrotic enteritis in both natural outbreaks and experimental models include: (a) coccidiosis, (b) migration of parasitic larvae, (c) feeds high in fish meal or wheat, and (d) immunosuppressive diseases. In addition, necrotic enteritis can be experimentally reproduced by: (i) providing animals feed contaminated by C. perfringens, (ii) administering animals vegetative cultures orally or into the crop, or (iii) intraduodenal administering of broth cultures of bacteria-free crude toxins to the animals.

C. perfringens Types A or C are the two biotypes that cause necrotic enteritis in poultry, with alpha toxin being the most common toxin detected [Wages and Opengart, Necrotic Enteritis. pp: 781-785, In: Disease of Poultry, 11$^{th}$ ed., (eds., Saif et al.), Iowa State Press, Ames, Iowa (2003)]. Indeed, greater than 90% of the C. perfringens isolates obtained from forty-two Type A infected fowl produced a lethal alpha toxin, along with sialidase, and the theta and mu toxins [Daube et al., AJVR 54:496-501 (1996)]. In addition, enterotoxin produced by C. perfringens Type A has been identified in chickens with necrotic enteritis and may play a role in the intestinal disease [Niilo, Can. J. Comp. Med. 42:357-363 (1978)].

Recently, it has been reported that C. perfringens Type A or Type C can encode the cpb2 gene [Gilbert et al., Gene 203:56-73 (1997)] and express its product, the beta 2 toxin. A strong correlation between the expression of beta 2 toxin and neonatal enteritis in swine has been observed [Bueschel et al., Vet Micro 94:121-129 (2003)]. The beta 2 toxin also has been implicated as a pathogenic factor in enteritis of horses and cattle. Bueschel et al., supra, further reported that 37.2% of the three thousand and twenty C. perfringens isolates that they obtained encoded the beta 2 toxin, and of the C. perfringens Type A isolates examined, 35.1% encoded the beta 2 toxin. The limited sample (n=5) of avian C. perfringens Type A field isolates were found to be ≈35% positive for the cpb2 genotype, and 40% of these also expressed the beta 2 toxin. In addition, employing PCR, Engstrom et al., [Vet Micro 94:225-235 (2003)] found that 12% of the C. perfringens isolates from chickens with hepatitis also were positive for cpb2. The enterotoxin of C. perfringens Type A has also been shown to be pathogenic in chickens, causing accumulation of fluid in a ligated intestinal loop model [Niilo, Appl. Micro. 28:889-891 (1974)].

Current efforts to control C. perfringens rely upon sanitary measures and placing antibiotics in the animal feed. The clostridial component of the disease responds well to antibiotics and is generally suppressed by antibiotic feed additives and ionophorous, anticoccidial drugs. However, antibiotics are costly and subject to increasing concerns related to the promotion of bacterial resistance.

Vaccination also has become an important control measure in domestic animals, since the course of many C. perfringens-associated diseases is rapid and often fatal. For example, U.S. Pat. No. 4,292,307 defines one "universal"

multivalent vaccine prepared from toxoids of *C. perfringens* Type A, Type B, and Type D that further includes toxoids from *Cl. oedematiens*, and *Cl. septicum* toxoid. In addition, vaccines are commercially available that are often multivalent and consist of inactivated cells, toxins, or combinations of these two [see, Songer, *Clin. Micro. Rev,* 9(2):216-234 (1996)].

Vaccination of female livestock may also elicit passive protection of their subsequently born offspring. Passive protection of mammalian neonates against pathologic Clostridial infections relies upon the transfer of specific antibody in the form of colostral antibodies. For example, Smith and Matsuoka [*Am. J. Vet. Res.* 20:91-93 (1959)] employed an inactivated vaccine to inoculate pregnant sheep and reported maternally induced protection of young lambs against the epsilon toxin of *C. perfringens*. Passive immunity in young mammals typically lasts 2 to 3 weeks [Songer, *Clin. Micro. Rev,* 9(2):216-234 (1996)].

In contrast to suckling mammals, passive immunity in avians has several obvious shortcomings, most notably, the complete lack of the maternal antibodies obtained from milk. Though passive immunity is just one possible explanation for their observed correlation, Heier et al., [Avian Diseases 45:724-732 (2001)] did report that the survival of chicks was significantly higher in Norwegian Broiler flocks having higher titers of specific, naturally occurring maternal antibodies against *C. perfringens* alpha toxin than those flocks having low titers. In addition, Lovland et al. [*Avian Pathology* 33(1):83-92 (2004)] reported results that were consistent with modest passive protection of the progeny of hens that had been inoculated with vaccines based on *C. perfringens* Type A or Type C toxoids, as compared to the progeny of unvaccinated hens.

Heretofore, commercially significant protection from *C. perfringens* did not appear be attainable unless maternal antibodies for most, if not all of the pathologic components produced by *C. perfringens* bacteria were present in the inoculum. For example, vaccination of the dam with a product that does not contain enterotoxin only offers partial protection to piglets, and anti-epsilon toxin antibody in mother goats protects against death from toxemia, but not against enterocolitis [Songer, *Clin. Micro. Rev,* 9(2):216-234 (1996)].

Indeed, despite the tabulation of an impressive quantity of data regarding the various biotypes of *C. perfringens* and their corresponding toxins and deleterious bioactive substances, clostridial diseases in food producing animals remain a significant economic problem for farmers. Therefore, there is a need to provide additional means for protecting livestock against the pathological effects of *C. perfringens*. More particularly, there remains a need to provide a safe and effective vaccine against *C. perfringens* in poultry. Moreover, there is a need to provide a simple vaccine against *C. perfringens* that can be administered to female animals, especially fertile and/or pregnant female livestock, that will passively protect their offspring.

The citation of any reference herein should not be construed as an admission that such reference is available as "prior art" to the instant application.

SUMMARY OF THE INVENTION

The present invention provides vaccines against *C. perfringens* that comprise a *C. perfringens* alpha toxoid, and/or an antigenic fragment of a *C. perfringens* alpha toxoid, and/or an inactive antigenic fragment of a *C. perfringens* alpha toxin, and/or any combination thereof as an antigen.

The present invention further provides vaccines that consist essentially of a single *C. perfringens* Type alpha toxoid, and/or an antigenic fragment of a *C. perfringens* alpha toxoid, and/or an inactive antigenic fragment of a *C. perfringens* alpha toxin, and/or any combination thereof as an antigen.

Preferably, one to two doses of 0.25-0.6 mL per dose of a vaccine of the present invention is sufficient to induce at least four antitoxin units (A.U.) of anti-alpha toxin antibody per mL of antisera of an animal (e.g., a chicken) vaccinated with the vaccine. In one embodiment of this type, the determination of antitoxin units (A.U.) of anti-alpha toxin antibody per mL of antisera of an animal vaccinated with the vaccine is performed six to seven weeks following the immunization. In a particular embodiment, a single dose of the vaccine is sufficient to induce at least 4 antitoxin units (A.U.) of anti-alpha toxin antibody per mL of antisera of the vaccinated animal, whereas, in an alternative embodiment, two doses of the vaccine are necessary. In a one embodiment the antigen has 2 or more Total Combining Power units (TCP).

In one such embodiment the animal is an avian. In a particular embodiment, the avian is a chicken. In another embodiment, the avian is a turkey.

In one embodiment, the antigen originated from a *C. perfringens* Type A cell, e.g., a *C. perfringens* Type A alpha toxoid. In another embodiment the antigen originated from a *C. perfringens* Type C cell, e.g., an inactive antigenic fragment of a *C. perfringens* Type C alpha toxin. In yet another embodiment the antigen originated from *C. perfringens* Type B. In still another embodiment the antigen originated from *C. perfringens* Type D. In yet another embodiment, the antigen originated from *C. perfringens* Type E. In still another embodiment, the vaccine comprises an antigen originating from a *C. perfringens* sub-type.

In one embodiment, a vaccine of the present invention comprises an antigen that is a single *C. perfringens* Type antigen, with the proviso that only a single *C. perfringens* Type antigen is present in that vaccine. In one particular embodiment of this type, the *C. perfringens* is Type A. In a related embodiment, the *C. perfringens* is Type C. In one embodiment the antigen is an alpha toxoid. In a particular embodiment of this type, the alpha toxoid is comprised by a *C. perfringens* alpha toxoid supernatant. In a specific embodiment, the vaccine comprises an alpha toxoid supernatant of a single *C. perfringens* Type, Type A.

In one vaccine of the present invention, the antigen is an alpha toxoid of an alpha toxin naturally encoded by a *C. perfringens* cell. In another vaccine of the present invention, the antigen is a recombinant polypeptide, i.e., one that is encoded by a gene that had been genetically manipulated. In an embodiment of this type, the recombinant polypeptide is an alpha toxoid in which enzymatic regions of the corresponding alpha toxin had been genetically removed or altered, but, one or more antigenic epitopes had been retained.

In a particular embodiment the antigen is in a whole cell preparation. In another embodiment, the antigen is in a cell-free preparation. In yet another embodiment, the antigen is an alpha toxoid in a *C. perfringens* alpha toxoid supernatant. In a particular embodiment of this type, the *C. perfringens* alpha toxoid supernatant also is a cell-free preparation.

In another aspect of the present invention, a vaccine may also contain multiple antigens which may result in the production of antibodies of a variety of specificities when administered to an animal subject. Not all of these antibodies need to be protective against a disease. In a particular embodiment of this type, such antigens are also from *C. perfringens*. Thus, a vaccine of the present invention may contain various other active or inactivated pathogenic factors, along with an alpha toxoid. Therefore, in accordance with the present invention, the alpha toxoid can be combined with other clostridial and non-clostridial cells, toxoids, and extracts, as well as inactive antigenic fragments of alpha toxin.

One such multivalent vaccine of the present invention comprises a *C. perfringens* alpha toxoid, and/or an antigenic fragment of a *C. perfringens* alpha toxoid, and/or an inactive antigenic fragment of a *C. perfringens* alpha toxin, and/or any combination thereof, and further comprises a viral antigen and/or a bacterial antigen and/or a parasite antigen. In a particular embodiment of this type the viral source of the antigen is infectious bursal disease virus. In another embodiment, the viral source of the antigen is infectious bronchitis virus. In yet another embodiment, the viral source of the antigen is reovirus. In still another embodiment, the viral source of the antigen is Newcastle disease virus. In yet another embodiment, the bacterial source of the antigen is *E. coli*. In still another embodiment, the bacterial source of the antigen is *Salmonella*. In yet another embodiment, the bacterial source of the antigen is *Campylobacter*. In still another embodiment the parasitic source of the antigen is from *Eimeria*. In a particular embodiment of this type, the antigen employed in the vaccine is a part of an *Eimeria* merozoite, an *Eimeria* oocyst, or a mixture thereof. In a related embodiment the natural host of the parasite is an avian. In a particular embodiment of this type the parasite is *Eimeria* and the natural host of the parasite is a chicken.

A multivalent vaccine of the present invention can also comprise one or more of the following antigens: *C. perfringens* beta toxin, *C. perfringens* beta 2 toxin, *C. perfringens* enterotoxin, *C. perfringens* epsilon toxin, *C. perfringens* iota toxin, *C. perfringens* kappa toxin, *C. perfringens* lambda toxin, *C. perfringens* theta toxin, *C. sordellii* hemorrhagic toxin, *C. sordellii* lethal toxin, *C. difficile* A toxin, *C. difficile* B toxin, *C. septicum* alpha toxin, *C. novyi* alpha toxin, and *C. novyi* beta toxin.

In a particular multivalent vaccine of the present invention, the vaccine comprises a *C. perfringens* alpha toxoid, and/or an antigenic fragment of a *C. perfringens* alpha toxoid, and/or an inactive antigenic fragment of a *C. perfringens* alpha toxin, and/or any combination thereof, and further comprises one or more viral antigens from infectious bursal disease virus, and/or infectious bronchitis virus and/or reovirus, and/or Newcastle disease virus, and/or bacterial antigens from *E. coli*, and/or *Salmonella*, and/or *Campylobacter*; and/or a parasitic antigen from *Eimeria*.

In an alternative embodiment, a multivalent vaccine of the present invention consists essentially of a single *C. perfringens* Type alpha toxoid, and/or an antigenic fragment of a *C. perfringens* alpha toxoid, and/or an inactive antigenic fragment of a *C. perfringens* alpha toxin, and/or any combination thereof. In a related embodiment, the vaccine further contains a viral antigen and/or a bacterial antigen and/or a parasitic antigen, as provided herein.

A vaccine of the present invention can also comprise an adjuvant. One popular animal adjuvant is an aluminum hydroxide adjuvant. An alternative adjuvant can be comprised in a water-in-oil emulsion along with the antigen. In a particular vaccine of this type, the water-in-oil emulsion is prepared with a 70% oil phase and a 30% aqueous phase. In another embodiment, the adjuvant is specifically not an aluminum hydroxide adjuvant. In one such embodiment, the vaccine including a non-aluminum hydroxide adjuvant is administered to poultry. In a particular embodiment, a vaccine comprises a *C. perfringens* alpha toxoid, an adjuvant, and one or more protective antigens, either recombinant or natural, obtained from a virus, bacterium, and/or a bacterial extract.

In another aspect, the present invention provides methods of providing active immunity to an avian by immunizing an avian with a vaccine of the present invention. In a particular embodiment the vaccine dosage for such active immunity is about 0.05 to about 0.1 mL. In one embodiment the avian is a turkey. In another embodiment the avian is a chicken. In still another embodiment the avian is a pheasant. The present invention also provides a method of administering a multivalent vaccine of the present invention to an avian to protect it against multiple diseases.

The present invention also provides methods of providing passive immunity to the progeny of a female animal (e.g., a pregnant female) comprising administering a vaccine of the present invention to the female animal (e.g., mother) prior to the birth of her progeny. In one embodiment, the female is an avian and the vaccine is administered to the avian female prior to her laying of the eggs that comprise the progeny. In this manner her progeny are provided passive immunity. In one such embodiment, the avian is a chicken. In another embodiment, the avian is a turkey. In still another embodiment, the avian is a pheasant.

In a particular embodiment, the method provides passive immunity against a clostridial disease to the progeny of the vaccinated animal. In one such method the clostridial disease is a clostridial enteric disease. In a particular method of this type, the clostridial enteric disease is necrotic enteritis. In another such method the clostridial disease is cholangiohepatitis. In still another embodiment the method provides passive immunity against a clostridial disease to the progeny of the vaccinated animal as well as provides protection against gangrenous dermatitis, septicum, and/or hepatitis.

In one embodiment, the method of providing passive immunity to the progeny of a female animal comprises administering a multivalent vaccine to the female animal to protect her progeny against multiple diseases. In a particular embodiment of this type, the female animal is in the poultry family and her progeny are protected from multiple poultry diseases.

In a particular embodiment the dosage for providing passive immunity to the progeny of a female animal is about 0.25 mL per dose of the vaccine. In another embodiment the dosage is about 0.4 mL per dose of the vaccine. In still another embodiment the dosage is about 0.6 mL per dose of the vaccine. In an embodiment exemplified below, the dosage is about 0.5 mL per dose of the vaccine.

The present invention further provides a process for making a *C. perfringens* alpha toxoid vaccine of the present invention. One such method comprises growing a *C. perfringens* cell in a culture medium to produce a quantity of cultured cells that secrete a *C. perfringens* alpha toxin into the cell medium. The *C. perfringens* alpha toxoid is then produced by inactivating the secreted alpha toxin. A majority of the cultured cells are removed from the culture medium to form a *C. perfringens* alpha toxoid supernatant. In a particular embodiment of the method, the concentration of the *C. perfringens* alpha toxoid supernatant is adjusted so that it is sufficient to induce at least four antitoxin units (A.U.) of anti-alpha toxin antibody per mL of antisera of an animal (e.g., a chicken) that has been vaccinated with either one or two doses of 0.25-0.6 mL per dose of said vaccine. In one such embodiment, the concentration process includes diafiltration against a buffered solution in order to remove low molecular weight contaminants.

The process for making a *C. perfringens* alpha toxoid vaccine of the present invention can further comprise mixing the *C. perfringens* alpha toxoid supernatant with an adjuvant. In one such embodiment, the *C. perfringens* alpha toxoid supernatant is mixed in a water-in-oil emulsion. In a particular embodiment of this type, the water-in-oil emulsion is prepared with 70% oil phase and 30% aqueous phase.

The *C. perfringens* cells employed in the process can be from a single *C. perfringens* Type cell. In a particular embodiment of this type, the single *C. perfringens* Type cell is a *C. perfringens* Type A cell. In an alternative embodiment, the single *C. perfringens* Type cell is a *C. perfringens* Type C cell.

These and other aspects of the present invention will be better appreciated by reference to the following Detailed Description.

DETAILED DESCRIPTION OF THE INVENTION

The present invention provides unique vaccines against *C. perfringens* that are both safe and effective for the prevention of clostridial diseases in animals. In a particular embodiment, the administration of a vaccine of the present invention to a female animal subject results in both the immunization of the female animal, and the development of antibodies that can be passively transferred to her subsequently born progeny. In one embodiment the present invention provides a vaccine that comprises a specific, minimum amount of an alpha toxoid of a single *C. perfringens* Type that is effective against harmful *C. perfringens* infections. In a particular embodiment, the vaccine comprises a safe and immunologically effective combination of an alpha toxoid of the present invention and a pharmaceutically acceptable adjuvant.

The vaccines of the present invention can be used to protect against any condition or disease in which *C. perfringens* plays a role. Such diseases include clostridial diseases. In one embodiment of this type, the clostridial disease is a clostridial enteric disease. Therefore, in a particular embodiment, the present invention provides vaccines that are effective for the prevention of the clostridial enteric disease in poultry known as necrotic enteritis. Other disease syndromes also may be prevented by the vaccines of the present invention and include, but are not limited to, clostridia-related hepatitis, cholangeohepatitis, and grangrenous dermatitis.

The present invention discloses that a vaccine comprising a specific minimal amount of alpha toxoid (i.e., having a specific minimal TCP) obtained from a single *C. perfringens* Type, protects the progeny of the vaccinated female animal subject from clostridial diseases such as necrotic enteritis, regardless of whether any additional lethal toxins are expressed by a challenge *C. perfringens*. The present invention further discloses a vaccine that elicits a specific minimal anti-alpha toxin response from the vaccinated female animal, which also protects the progeny of that vaccinated female animal subject from clostridial diseases, regardless of whether any additional lethal toxins are expressed by a naturally occurring *C. perfringens*. The vaccines of the present invention also may be administered with an acceptable adjuvant.

As exemplified below, vaccinating hens with a vaccine derived from an inactivated *C. perfringens* Type A isolate that expresses an alpha toxin, but not a corresponding beta 2 toxin, unexpectedly, led to the passive immunization of the three week-old progeny chicks against a challenge from a *C. perfringens* strain that expressed both the alpha toxin and the beta 2 toxin. Heretofore, there had been no evidence for such cross-protection against these two distinct toxins. Therefore, the present invention provides relatively simple vaccines that are capable of stimulating a specific minimum amount of anti-alpha toxins and thereby, protect against clostridial diseases, e.g., necrotic enteritis, regardless of what other toxins the *C. perfringens* challenge strain may express.

Indeed, in spite of the multitude of toxins and other biologically active proteins produced by *C. perfringens* that have been shown to have pathogenic effects on animals, and the multiple citations in the literature on the contributions of these various toxins and other proteins to the pathology of necrotic enteritis, the unique vaccines disclosed herein provide both a substantial immune response to *C. perfringens* in vaccinated broiler hens, and passive immunity to their subsequently born offspring.

Although the present invention is completely independent of any theory or model, the results provided herein are consistent with the *C. perfringens* alpha toxin being the antigenic component that is both necessary and sufficient for protection against necrotic enteritis. While the beta, beta 2 and enterotoxins may be critical to the pathology of necrotic enteritis, the results provided herein are consistent with the alpha toxoid being the only toxoid necessary in a vaccine for necrotic enteritis. In addition, since alpha toxin production is generally the highest in Type A strains, *C. perfringens* Type A strains are particularly useful as a source of *C. perfringens* alpha toxin. However, other *C. perfringens* Types also can be successfully used, especially when genetic modification has been used to increase the level of alpha toxin production in these other Types.

As used herein the following terms shall have the definitions set out below: As used herein a "protective antigen" is an antigen that results in the production of specific antibodies that impart protection against infection and/or disease to the animal vaccinated with that antigen and/or her progeny. A vaccine which contains such a protective antigen is termed "immunologically effective".

As used herein the term "antigenic fragment" in regard to a particular protein is a fragment of that protein that is antigenic. For example, an antigenic fragment of an alpha toxin or an alpha toxoid is a fragment of the alpha toxin or alpha toxoid that is antigenic. As used herein, an antigenic fragment of an alpha toxin or an alpha toxoid can be any fragment of the alpha toxin or alpha toxoid, respectively, including large fragments that are missing as little as a single amino acid from the full-length protein. In a particular embodiment an antigenic fragment of an alpha toxin or alpha toxoid contains between 6 and 120 amino acid residues. In addition, an antigenic fragment of a given alpha toxin can be obtained by a recombinant source, from a protein isolated from natural sources, or through chemical synthesis. Moreover, an antigenic fragment can be obtained following the proteolytic digestion of an alpha toxin, alpha toxoid, or a fragment thereof, through recombinant expression, or alternatively, it can be generated de novo, e.g., through peptide synthesis.

As used herein an "inactive antigenic fragment" of a *C. perfringens* alpha toxin is an antigenic fragment of a *C. perfringens* alpha toxin that retains at least one antigenic epitope, but does not possess sufficient catalytic activities of the alpha toxin to make it deleterious. Such inactive antigenic fragments may be used alone, or alternatively, can be incorporated into fusion proteins.

As used herein, the term "alpha toxoid" refers to any inactive alpha toxin, (e.g., an inactive full-length alpha toxin) but is not meant to limit in any way the particular means of inactivating an alpha toxin to produce that alpha toxoid. Such inactivating methodology includes: (i) chemical methods that modify the intact protein, e.g., formaldehyde or glutaraldehyde treatment; (ii) physical methods, such as heating; (iii) enzymatic methods that alter the protein, such as a protease that cleaves the toxin into fragments; (iv) recombinant methods, such as genetic engineering of the alpha toxin gene to remove or alter enzymatic regions of the protein, but retaining one or more antigenic epitopes (see e.g., U.S. Pat. No. 5,817,317, the contents of which is hereby incorporated by reference in its entireties); and/or combinations of any or all of the above.

As used herein a *C. perfringens* "alpha toxoid supernatant" is a solution comprising inactivated *C. perfringens* alpha toxin, in which at least a majority of the cells that produced the toxin have been removed (i.e., greater than 70% of the cells being removed, and in a particular embodiment, greater than 90% of the cells being removed). In a particular embodiment, the inactivated *C. perfringens* alpha toxin had been secreted into the culture media by *C. perfringens* cells that had been added to and/or cultured/grown in that culture media, and then inactivated. In another embodiment, the inactivated *C. perfringens* alpha toxin includes the *C. perfringens* alpha toxin associated with the cells, which had been liberated through cell lysis, and then inactivated. The means of preparing the "alpha toxoid supernatant" is in no way meant to be limited to any particular method of removing the cells or cell debris from the solution, and includes centrifugation, column chromatograpy, ultrafiltration, etc.

As used herein a "cell-free" solution is one in which greater than 90% of the cells from a culture have been removed. The means of preparing the "cell-free" solution is in no way meant to be limited to any particular method of removing the cells or cell debris from the solution, and includes centrifugation, column chromatography, ultrafiltration, etc.

As used herein the term "single *C. perfringens* Type" refers to one *C. perfringens* Type, e.g., Type A or Type B or Type C etc., as opposed to multiple Types, e.g., Type A and Type B and Type C. Therefore, a cell, supernatant, composition, preparation, vaccine, etc. comprising an alpha toxoid of a "single *C. perfringens* Type" is a cell, supernatant, composition, preparation, vaccine, etc. that contains alpha toxoid from only that one specific *C. perfringens* Type and does not contain alpha toxoid from any other *C. perfringens* Type. On the other hand, such cells, supernatants, compositions, preparations, vaccines, etc. may contain other non-alpha toxoid components, including other *C. perfringens* toxoids, and/or adjuvants, and/or immune stimulants, etc.

As used herein an "antitoxin unit" or "A.U." of anti-alpha toxin antibody per mL of antisera is used interchangeably with "anti-alpha Toxin Neutralizing Test" units or "TNT" units and is defined by the ability of sera to neutralize the toxic effects of alpha toxin in a mouse bioassay. In this test, a known amount of alpha toxin established by international standards [EU Pharmacopoeia 5.0.: 01/2005:0088, pp. 803-804] is mixed with serial dilutions of sera from vaccinated animals. The mixture is incubated one hour at room temperature and then injected intravenously into mice. The mice will survive if the toxin is completely neutralized by the sera, otherwise they die. The antitoxin units or titer is determined as the reciprocal of the highest dilution of sera that neutralized the toxin.

As used herein the term "Total Combining Power" is abbreviated by "TCP" and is defined as described by Batty [*Toxin-Antitoxin Assay, Methods in Microbiology*, Chapter 8, Volume 5A (1971), ed. JR Norris and DW Ribbons]. In this assay, a specific volume of the alpha toxoid supernatant is contacted with a known quantity of antitoxin units. After providing a suitable incubation period to allow the antitoxin and alpha toxoid to bind, e.g., one hour at room temperature, a known quantity of the alpha toxin is added. The remaining free antitoxin then is given a suitable period to bind with the alpha toxin, e.g., one hour at room temperature. The amount of free alpha toxin is then determined by adding a substrate to the solution to measure the enzymatic activity of the alpha toxin. Suitable substrates include red blood cells (particularly sheep red blood cells) and lecithin. The alpha toxoid can then be quantified through a calculation based upon the amount of enzymatic activity determined. The greater the amount of alpha toxoid present in the assay solution, the higher the amount of enzymatic activity measured in the assay.

The terms "Type" and "biotype" are used interchangeably herein, and refer to the particular phenotype of a *C. perfringens* based on expression of various toxin genes. *Clostridium perfringens* is divided into types based on production of the four major toxins, alpha, beta, epsilon and iota. *C. perfringens* Type A produces alpha toxin; Type B produces alpha, beta and epsilon toxins; Type C produces alpha and beta toxins, Type D produces alpha and epsilon toxins, Type E produces alpha and iota toxins. As many as 17 exotoxins of *C. perfringens* have been described. A biotype of *C. perfringens* is a classification based on production of some or all of the additional clostridial toxins and/or enzymes. For examples an enterotoxigenic pathotype of *C. perfringens* Type A may produce theta and mu toxins in addition to the alpha toxin.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens. An adjuvant may be administered to the target animal before, in combination with, or after the administration of the vaccine. Adjuvants of the present invention may be obtained from any of a number of sources including from natural sources, recombinant sources, and/or be chemically synthesized, etc. Examples of chemical compounds used as adjuvants include, but are not limited to aluminum compounds, metabolizable and non-metabolizable oils, block polymers, ISCOM's (immune stimulating complexes), vitamins and minerals (including but not limited to: vitamin E, vitamin A, selenium, and vitamin B12), Quil A (saponins), and CARBOPOL®. Additional examples of adjuvants, that sometimes have been referred to specifically as immune stimulants, include, bacterial and fungal cell wall components (e.g., lipopolysaccarides, lipoproteins, glycoproteins, muramylpeptides, beta-1, 3/1,6-glucans), various complex carbohydrates derived from plants (e.g., glycans, acemannan), various proteins and peptides derived from animals (e.g., hormones, cytokines, co-stimulatory factors), and novel nucleic acids derived from viruses and other sources (e.g., double stranded RNA, CpG). In addition, any number of combinations of the aforementioned substances may provide an adjuvant effect, and therefore, can form an adjuvant of the present invention.

As used herein an "anti-alpha toxin" is an antibody (monoclonal or polyclonal) that binds to alpha toxin. Antibodies to an alpha toxin can be measured by a TNT assay as described above. Alternatively, antibodies can be detected by their ability to block the hemolytic effect of the alpha toxin. In a hemolysis inhibition assay, a known quantity of alpha toxin, sufficient to catalyze complete lysis of a given preparation of sheep red blood cells, is mixed with serial dilutions of sera and incubated for one hour at 36±2° C. The mixture is then incubated with 0.5% sheep red blood cells for three hours at 36±2° C. When antibody binds to the alpha toxin, the toxin is unable to hemolyze the red blood cells. The titer is determined by the reciprocal of the highest dilution of sera that results in no hemolysis. In a similar assay, the ability of antibodies bound to alpha toxin to inhibit phospholipase activity can be measured by determining the highest dilution of antisera that blocks the enzymatic cleavage of lecithin.

As used herein the term "polypeptide" is used interchangeably with the term "protein" and is further meant to encompass peptides. Therefore, as used herein, a polypeptide is a polymer of two or more amino acids joined together by peptide linkages. Polypeptides of the present invention include naturally occurring proteins; recombinant proteins; chemically synthesized proteins; fragments of any of the naturally occurring, recombinant, or chemically synthesized proteins; and fusion proteins that comprise any of the naturally occurring, recombinant, and/or chemically synthesized proteins, and/or any of their fragments. Preferably, the term polypeptide is used to denote a polymer comprising twenty or more amino acid residues joined together by peptide linkages, whereas the term peptide is used to denote a polymer comprising two to twenty amino acid residues joined together by peptide linkages.

A "heterologous nucleotide sequence" as used herein is a nucleotide sequence that is added by recombinant methods to a nucleotide sequence encoding a protein of the present invention, e.g., an alpha toxin of the present invention, or encoding a fragment thereof (e.g., an inactive antigenic fragment), to form a nucleic acid that is not naturally formed in nature. Such nucleic acids can encode fusion proteins. In addition, as used herein, a heterologous nucleotide sequence need not be a single contiguous nucleotide sequence, but can include multiple non-contiguous nucleotide sequences that have been combined with a nucleotide sequence encoding a polypeptide of the present invention, or a portion thereof. A heterologous nucleotide sequence can comprise non-coding sequences including restriction sites, regulatory sites, promoters and the like. In still another embodiment the heterologous nucleotide can function as a means of detecting a nucleotide sequence of the present invention. The present invention provides heterologous nucleotide sequences that when combined with nucleotide sequences encoding a polypeptide of the invention or a fragment thereof, are necessary and sufficient to encode all of the fusion proteins of the present invention.

As used herein a vaccine "consisting essentially of" or that "consists essentially of" a single *C. perfringens* Type alpha toxoid, and/or antigenic fragment of the *C. perfringens* alpha toxoid, and/or inactive antigenic fragment of the corresponding alpha toxin is a vaccine that contains an immunologically effective amount of the single *C. perfringens* Type alpha toxoid, and/or antigenic fragment of the *C. perfringens* alpha toxoid, and/or inactive antigenic fragment of the corresponding alpha toxin, to protect against a clostridial disease, but does not contain an immunologically effective amount of any other antigen known to protect against a clostridial disease such as another *C. perfringens* antigen, or an alternative *C. perfringens* Type alpha toxin, alphatoxoid, or fragment thereof. Such vaccines may further include antigens related to other diseases such as viral antigens from infectious bursal disease virus, reovirus, and Newcastle disease virus; bacterial antigens from *E. coli, Salmonella*, and *Campylobacter*; and a parasite antigens such as one from *Eimeria*.

As used herein the term "about" when used in conjunction with a particular dosage value signifies that the dosage value is within twenty percent of the indicated value, e.g., a dosage of about 0.5 mL can comprise between 0.4 mL and 0.6 mL.

Isolation of *C. Perfringens* Type A

*C. perfringens* isolates, such as *C. perfringens* type A, can be obtained from fecal samples and/or intestinal scrapings of infected animals. The samples/scraping can be streaked on blood agar plates, incubated anaerobically at 35±1° C. for 24-48 hours, and colonies that resemble *C. perfringens* type A are individually picked. To confirm their identity as *C. perfringens* type A isolate(s), the selected colonies can be further tested for characteristic *C. perfringens* type A biochemical properties, including genetic makeup.

The presence of the alpha toxin gene in the isolate can be determined by genetic analysis, e.g., by PCR. The expression of alpha toxin can be shown by its lecithinase activity in an assay using egg yolk and/or by a hemolysis assay employing sheep red blood cells. In a particular embodiment, *C. perfringens* isolates that express a high level of alpha toxin are used in the preparation of a vaccine of the present invention. A selected *C. perfringens* isolate(s) can be grown anaerobically in nutrient broth for 4-24 hours. The culture can be inactivated with, e.g., formalin, concentrated and blended into such a vaccine.

*C. Perfringens* Toxins

Alpha Toxin—Alpha toxin is produced by all types of *C. perfringens*. Alpha toxin is a multifunctional phospholipase C that can split lecithin, forming phosphorylcholine and a diglyceride. When administered intravenously, alpha toxin has been shown to be lethal to mice. Alpha toxin is also markedly hemolytic. However, the susceptibility of red blood cells can vary greatly depending on the species of animal used as the source of the red blood cells. Alpha toxin also brings about the aggregation of platelets, the lysis of platelets, leukocytes, and other body cells, as well as causing an increase in vascular permeability.

Beta Toxin—Beta toxin is produced by *C. perfringens* Types B and C. The beta toxin is responsible for the inflammation of the intestine and the wholesale loss of mucosa, as well as the inhibition of intestinal movement. The beta toxin is a protein having a molecular weight of 35 kDa and is much more susceptible to proteolytic enzymes such as trypsin, than the other *C. perfringens* toxins. Beta toxin has been reported to be lethal to animals, with mice being the most sensitive and chickens being the least sensitive.

Beta 2 Toxin—The beta 2 toxin is the most recently discovered of the *C. perfringens* toxins. Despite their similar names, the amino acid sequences of the beta 2 toxin and the beta toxin show no homology. The literature has shown a strong association between beta 2 toxin and necrotic enteritis in certain animals [Garmory et al., *Epidemiol. Infect.*

124:61-67 (2000), Herholz et al., *J. Clin. Morco*, February: 358-361 (1999)]. The beta 2 toxin has a molecular weight of 28 kDa. Beta 2 toxin has been found to be lethal to mice and cytotoxic to certain cell lines, inducing rounding of the cells and lysis without affecting the actin cytoskeleton [Manteca et al., *Vet. Microb.* 86:191-202 (2002), Schotte et al., *J. Vet Med B* 51:423-416 (2004), Gilbert et al., *Gene* 203:65-73 (1997)].

Enterotoxin—Enterotoxin is typically produced by *C. perfringens* Type A strains. The presence of the enterotoxin has been traditionally used to delineate enteric disease associated strains from those which are associated with tissue gas gangrene. Strains which cause gas gangrene do not typically have enterotoxin. The enterotoxin is a heat sensitive protein that has a molecular weight of 34 kDa. The lethal dose for mice is about 10 micrograms. The initial interaction of the enterotoxin is to form pores in the host cell, followed by altered permeability of the cell, inhibition of macromolecular synthesis, cytoskeletal disintegration, and finally, lysis [see, Songer, *Clin. Micro. Rev,* 9(2):216-234 (1996)]. Enterotoxin effectuates the reversal of net transport in the cells of the intestines.

Epsilon Toxin—Epsilon toxin is produced by *C. perfringens* Types B and D. Epsilon toxin is secreted as a protoxin that is converted by endogenous trypsin into an extremely potent neurotoxin. When administered intravenously, Epsilon toxin can be extremely lethal to mice. Epsilon toxin has a high affinity for neural tissue and has the effect of causing vascular permeability. Epsilon toxin also causes permeability of the gut wall allowing large molecules, including itself, to enter the bloodstream. The epsilon toxin then progresses through the bloodstream to the brain where it disrupts the osmotic balance. This disruption of osmotic balance in the brain results in the neurological signs observed prior to the death of the afflicted animal.

Kappa Toxin—Kappa toxin is a collagen-hydrolyzing enzyme produced by *C. perfringens* Types A, D, E, and some Types of B and C. Kappa toxin has a molecular weight of 80 kDa and is lethal to mice. Intravenous injection of kappa toxin to a mouse produces death within one hour due to the intense hemorrhaging of the lungs.

Theta Toxin—Most strains of *C. perfringens* produce theta toxin. Theta toxin is 74 kDa protein responsible for the clear zones of hemolysis seen around colonies on blood agar plates. Purified theta toxin is extremely lethal to mice, producing death in a matter of minutes. Theta toxin is inhibited by certain steroids, with cholesterol being the most potent inhibitor.

Passive Immunity

The present invention includes a vaccine comprised of a safe and immunologically effective preparation of a minimum amount of an antigen of the present invention, e.g., an alpha toxoid, for the vaccination of non-human females, particular fertile and/or pregnant females, who can then transfer the effect of the vaccine to their newborn. Such transfer of immunity from mother to progeny is termed "passive immunity". Passive immunity can be accomplished inter alia through the ingestion of colostrums, as occurs in mammals or the absorption of antibody into the bloodstream from the egg yolk, as occurs in poultry. In addition, as disclosed herein, poultry may consume antibodies in ovo, which results in raising the level of circulating systemic antibodies.

As demonstrated herein, passively transferring a specific amount of anti-alpha toxin to the neonatal animal protects neonates against a virulent *Clostridium perfringens* challenge. The extent of protection, as disclosed below, was completely unexpected, as heretofore, it had been believed that the gut had to be bathed with antibodies in order to significantly protect against an oral *C. perfringens* type A challenge. Similarly, it is quite surprising that a correlation would exist between maternal antibody transfer of mucosal immunity through the ingestion of colostrum in the neonatal mammal and the absorption of maternal antibody in the egg. As demonstrated below for chickens, anti-alpha toxin antibodies are absorbed into the blood stream in ovo. Moreover, the present invention discloses that inducing a specific, defined minimum anti-alpha toxin antibody titer in the bloodstream of the hen is sufficient to protect the vaccinated offspring of that hen from a *C. perfringens* type A challenge performed weeks after the birth of those offspring.

Active Immunity

The present invention includes for the vaccination of chicken chicks (e.g., broiler chicks) and/or turkey poults to provide active immunity against necrotic enteritis, necrotic dermatitis and gangrenous dermatitis. The chicks and/or poults are vaccinated early in life, at about day one of age or slightly older (within the first week of life) with a single or two doses of the vaccine. Appropriate vaccine dosages for achieving active immunity can vary from about 0.05 mL to about 0.5 mL. In a particular embodiment the vaccine dosage is about 0.05 mL to about 0.1 mL.

Cell Culture

*Clostridium perfringens* secretes alpha toxin into the media during growth. After inactivation and removing at least a majority of the cells from the growth media, the resulting solution is referred to as an alpha toxoid supernatant. The cells are generally removed to minimize extraneous antigens in the vaccine which might otherwise promote reactivity and lessen the immune response. However, there is also a finite amount of cell-associated alpha toxin. Therefore, the alpha toxin antigen may be derived from the cells and/or the media, in either concentrated or non-concentrated form.

*C. perfringens* may be grown in any appropriate vessel including flasks, bottles, jugs, or mechanical fermenters. Fermentations may be monitored during growth so as to harvest the fermenter when the alpha toxin production is at its peak. Typical methods include affinity chromatography, gel electrophoresis (PHAST system, etc.), immuno assays, hemolysin and lecithinase activity assays. The cell culture fluid or cellular extract can be inactivated with formaldehyde (0.1-2.0%) or a combination of formaldehyde and heat. Other chemicals that are typically used for protein denaturing and may also be used include, but are not limited to: glutaraldehyde, phenol, various detergents such as Triton X-100, Sodium dodecyl sulfate (SDS), and alcohols. Residual formaldehyde levels may be monitored during inactivation so as to keep an optimal level without over or under toxoiding. Typical methods for measuring free formaldehyde are listed in the European Pharmacopoeia (01/2005:20418) or the 9 CFR (113.100). Similar methods are available for measuring other types of toxin inactivants. In certain instances the alpha toxin is deliberately under-toxoided at this point in order to minimize denaturation of epitopes critical for the development of antitoxins, and then further treated for detoxification at a later point in the process. Other suitable chemical or biological agents capable of inactivating the toxin may be also used such as glutaraldehyde, phenol, various detergents such as Triton X-100, Sodium dodecyl sulfate (SDS), and alcohols.

The resulting alpha toxoid may be stored for a period of time prior to any additional processing, without detrimental effects. Typically, optimal storage is at 2-8° C. However, inactivated clostridial toxoids are extremely stable and may also be stored at higher temperature. For periods of storage longer than 6 months and higher than 8° C. in temperature, it may be advisable to retest the potency of the toxoid by a Total Combining Power test (TCP), or another similar immunological assay to determine the immunogenic stability of the toxoid.

The cells may be removed from the inactivated culture medium by centrifugation and/or filtration to obtain the toxoid supernatent. Removal of the cells serves to reduce tissue reactivity that can be caused by the cell components, whereas, removing extraneous antigens from the preparation helps the immune response to focus on the toxoid component of the vaccine.

The inactivated culture medium may be concentrated by any of a number of means including ultrafiltration (preferably using ultrafiltration membranes of not greater than 30,000 molecular weight cut-off) or by lyophilization.

The concentration process may include diafiltration against an aqueous solution (e.g., phosphate buffered saline) in order to remove low molecular weight contaminants from the preparation. The concentrated fluid may be re-treated one or more times with either formaldehyde and/or heat until a suitable assay indicates that the fluid is free from residual toxicity. Such assays include a mouse bioassay, i.e., injecting the fluid into mice and observing its effect on the mice; or measuring hemolysin activity, or lecinthinase activity, etc.

The pH of the solution may have to be adjusted prior to blending to ensure optimal binding to adjuvants, emulsification with oils, and/or stability of solution. The isoelectric point (pI) of the alpha toxin is approximately 5.5 [Smith et al., *The Pathogenic Anaerobic Bacteria*, (3$^{rd}$ Ed.) Charles Thomas Publishers, p. 116 (1984)]. Adjustment of the pH of the toxoid solution will alter the net charge on the protein, which is advantageous for enhancement of binding to certain adjuvants, such as aluminum adjuvants. The pH may also be adjusted to a level which increases the stability of the alpha toxoid for storage over a prolonged period of time. For example, proteins are more likely to precipitate out of solution at their pI, but are usually stable at 1 pH unit above or below this value.

Nucleic Acids Encoding the Polypeptides of the Present Invention

A nucleic acid, such as a cDNA, that encodes a polypeptide of the present invention, can be used to generate recombinant bacterial host cells that express a protein and/or antigen of the present invention, e.g., the alpha toxin. Such recombinant host cells can be inactivated, i.e., converted to bacterins, and used in immunogenic compositions such as vaccines.

In addition, obtaining and/or constructing a nucleic acid that encodes a polypeptide of the present invention, including those encoding an alpha toxin of the present invention, or an inactive antigenic fragment thereof, may facilitate the production of the alpha toxin, alpha toxoid or fragments thereof. The alpha toxin, alpha toxoid and/or antigenic fragments of either are useful for making certain vaccines of the present invention.

Accordingly, the present invention includes nucleic acid constructs that allow for the expression and isolation of the proteins and/or antigenic fragments of the present invention. Sequences for such nucleic acids and corresponding recombinant proteins of the antigens to be used in this aspect of the present invention are well known to the skilled artisan. A small sampling of the antigens that can be used in the vaccines of the present invention, along with their GenBank accession number, and a scientific article disclosing their amino acid sequences are provided below.

| EXAMPLES OF ANTIGENS THAT CAN BE USED IN VACCINES | | |
|---|---|---|
| SOURCE Antigen | ACCESSION No. | [1]ARTICLE |
| *C. PERFRINGENS* | | |
| alpha toxin | CAA35186 | Saint-Joanis et al., Mol. Gen. Genet. 219 (3): 453-460 (1989) |
| beta toxin | CAA58246 | Steinthorsdottir et al., FEMS Microbiol. Lett. 130 (2-3): 273-278 (1995) |
| beta 2 toxin | NP_150010 | Shimizu et al., Proc. Natl. Acad. Sci. U.S.A. 99 (2): 996-1001 (2002) |
| enterotoxin | BAE79112 | Miyamoto et al., J. Bacteriol. 188 (4): 1585-1598 (2006) |
| epsilon toxin | AAA23236 | Havard et al., FEMS Microbiol. Lett. 97: 77-82 (1992) |
| iota toxin | CAA51959 | Perelle et al., Infect. Immun. 61 (12): 5147-5156 (1993) |
| kappa toxin | NP_561089 | Shimizu et al., Proc. Natl. Acad. Sci. U.S.A. 99 (2): 996-1001 (2002) |
| lambda toxin | CAA35187 | Saint-Joanis et al., Mol. Gen. Genet. 219 (3): 453-460 (1989) |
| theta toxin | NP_561079 | Shimizu et al., Proc. Natl. Acad. Sci. U.S.A. 99 (2): 996-1001 (2002) |
| *C. DIFFICILE* | | |
| A toxin | A37052 | Wren et al., FEMS Microbiol. Lett. 70: 1-6 (1990) |
| B toxin | CAA43299 | von Eichel-Streiber et al., Mol. Gen. Genet. 233: (1-2), 260-268 (1992) |
| *C. SEPTICUM* | | |
| alpha toxin | AAB32892 | Ballard et al., *Infect. Immun.* 63 (1): 340-344 (1995) |
| *C. NOVYI* | | |
| alpha toxin | AAB27213 | Ball et al., Infect. Immun. 61 (7): 2912-2918 (1993) |

[1]The sequences provided in these articles are hereby incorporated by reference.

The nucleic acids encoding protein antigens that can be used in the vaccines of the present invention can further contain heterologous nucleotide sequences. To express a recombinant protein of the present invention in a host cell, an expression vector can be constructed comprising the corresponding cDNA. The present invention therefore, includes expression vectors containing nucleic acids encoding recombinant proteins of the present invention, including variants thereof.

Due to the degeneracy of nucleotide coding sequences, other nucleotide sequences which encode substantially the same amino acid sequence as a nucleic acid encoding a polypeptide of the present invention may be used in the practice of the present invention. These include, but are not limited to, allelic genes, homologous genes from other strains, and/or those that are altered by the substitution of different codons that encode the same amino acid residue within the sequence, thus producing a silent change. Host cells comprising the expression vectors of the present invention are also included. One commonly employed host cell, is an *E. coli* cell.

General methods for the cloning of cDNAs and expression of their corresponding recombinant proteins have been described [see Sambrook and Russell, *Molecular Cloning, A laboratory Manual*, 3$^{rd}$ edition, Cold Spring Harbor Laboratory Press, Cold Spring Harbor L. I. (2000)].

In addition, any technique for mutagenesis known in the art can be used to modify a native alpha toxin of the present invention, including but not limited to, in vitro site-directed mutagenesis [Hutchinson et al., *J. Biol. Chem.*, 253:6551 (1978); Zoller and Smith, *DNA,* 3:479-488 (1984); Oliphant et al., *Gene,* 44:177 (1986); Hutchinson et al., *Proc. Natl. Acad. Sci.* U.S.A., 83:710 (1986); Wang and Malcolm, *BioTechniques* 26:680-682 (1999) the contents of which are hereby incorporated by reference in their entireties]. The use of TAB@ linkers (Pharmacia), etc. and PCR techniques also can be employed for site directed mutagenesis [see Higuchi, "Using PCR to Engineer DNA", in PCR Technology: Principles and Applications for DNA Amplification, H. Erlich, ed., Stockton Press, Chapter 6, pp. 61-70 (1989)].

Polypeptides of the Present Invention

The present invention includes isolated and/or recombinant polypeptides, including, the alpha toxins and alpha toxoids of the present invention, strain variants thereof, inactive antigenic fragments thereof, and fusion proteins thereof. In addition, polypeptides containing altered sequences in which functionally equivalent amino acid residues are substituted for those within the wild type amino acid sequence resulting in a conservative amino acid substitution are also included by the present invention.

For example, one or more of these amino acid residues within the sequence can be substituted by another amino acid of a similar polarity, which acts as a functional equivalent, resulting in a silent alteration. Substitutes for an amino acid within the sequence may be selected from other members of the class to which the amino acid belongs.

For example, the nonpolar amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine and lysine. The negatively charged (acidic) amino acids include aspartic acid and glutamic acid.

Particularly preferred conserved amino acid exchanges are:

(a) Lys for Arg or vice versa such that a positive charge may be maintained;

(b) Glu for Asp or vice versa such that a negative charge may be maintained;

(c) Ser for Thr or vice versa such that a free —OH can be maintained;

(d) Gln for Asn or vice versa such that a free NH$_2$ can be maintained; and (e) Ile for Leu or for Val or vice versa as roughly equivalent hydrophobic amino acids.

All of the polypeptides of the present invention, including the antigenic fragments, can be part of a fusion protein. In a specific embodiment, a fusion polypeptide is expressed in a prokaryotic cell. Such a fusion protein can be used for example, to enhance the antigenicity of an antigen or fragment thereof, to lower or remove its toxicity without negating its antigenicity, or to isolate an antigen of the present invention. Isolation of the fusion protein in the latter case can be facilitated through the use of an affinity column that is specific for the protein/peptide fused to the antigen. Such fusion proteins include: a glutathione-S-transferase (GST) fusion protein, a maltose-binding protein (MBP) fusion protein, a FLAG-tagged fusion protein, or a poly-histidine-tagged fusion protein. Specific linker sequences such as a Ser-Gly linker can also be part of such a fusion protein.

Indeed, the expression of a fusion polypeptide can facilitate stable expression, and/or allow for purification based on the properties of the fusion partner. Thus the purification of the recombinant polypeptides of the present invention can be simplified through the use of fusion proteins having affinity Tags. For example, GST binds glutathione conjugated to a solid support matrix, MBP binds to a maltose matrix, and poly-histidine chelates to a Ni-chelation support matrix [see Hochuli et al., *Biotechnology* 6:1321-1325 (1998)].

The fusion protein can be eluted from the specific matrix with appropriate buffers, or by treating with a protease that is specific for a cleavage site that has been genetically engineered in between an alpha toxin, for example, and its fusion partner. Alternatively, an alpha toxin can be combined with a marker protein such as green fluorescent protein [Waldo et al., *Nature Biotech.* 17:691-695 (1999); U.S. Pat. No. 5,625,048 and WO 97/26333, the contents of which are hereby incorporated by reference in their entireties].

Alternatively or in addition, other column chromatography steps (e.g., gel filtration, ion exchange, affinity chromatography etc.) can be used to purify the natural or recombinant polypeptides of the present invention (see below). In many cases, such column chromatography steps employ high performance liquid chromatography or analogous methods in place of the more classical gravity-based procedures.

In addition, the polypeptides of the present invention, including the alpha toxins and inactive antigenic fragments thereof can be chemically synthesized [see e.g., Synthetic Peptides: *A User's Guide*, W.H.Freeman & Co., New York, N.Y., pp. 382, Grant, ed. (1992)].

General Polypeptide Purification Procedures

Generally, initial steps for purifying a polypeptide of the present invention can include salting in or salting out, e.g., in ammonium sulfate fractionations; solvent exclusion fractionations, e.g., an ethanol precipitation. In addition, high speed ultracentrifugation may be used either alone or in conjunction with other extraction techniques.

Generally good secondary isolation or purification steps include solid phase absorption using calcium phosphate gel, hydroxyapatite, or solid phase binding. Solid phase binding may be performed through ionic bonding, with either an anion exchanger, such as diethylaminoethyl (DEAE), or diethyl[2-hydroxypropyll aminoethyl (QAE) SEPHADEX or cellulose; or with a cation exchanger such as carboxymethyl (CM) or sulfopropyl (SP) SEPHADEX or cellulose. Alternative means of solid phase binding includes the exploitation of hydrophobic interactions e.g., the use of a solid support such as phenylSepharose and a high salt buffer; affinity-binding immuno-binding, using e.g., an alpha toxin-antibody bound to an activated support. Other solid phase supports include those that contain specific dyes or lectins etc.

A further solid phase support technique that is often used at the end of the purification procedure relies on size exclusion, such as SEPHADEX and SEPHAROSE gels. Alternatively, a pressurized or centrifugal membrane technique, using size exclusion membrane filters may be employed. Oftentimes, these two methodologies are used in tandem.

Solid phase support separations are generally performed batch-wise with low-speed centrifugation, or by column chromatography. High performance liquid chromatography (HPLC), including such related techniques as FPLC, is presently the most common means of performing liquid chromatography. Size exclusion techniques may also be accomplished with the aid of low speed centrifugation. In addition size permeation techniques such as gel electrophoretic techniques may be employed. These techniques are generally performed in tubes, slabs or by capillary electrophoresis.

Almost all steps involving polypeptide purification employ a buffered solution. Unless otherwise specified, generally 25-100 mM concentrations of buffer salts are used. Low concentration buffers generally imply 5-25 mM concentrations. High concentration buffers generally imply concentrations of the buffering agent of between 0.1-2.0 M concentrations. Typical buffers can be purchased from most biochemical catalogues and include the classical buffers such as Tris, pyrophosphate, monophosphate and diphosphate and the Good buffers such as Mes, Hepes, Mops, Tricine and Ches [Good et al., *Biochemistry*, 5:467 (1966); Good and Izawa, *Meth. Enzymol.*, 24B:53 (1972); and Fergunson and Good, *Anal. Biochem.*, 104:300 (1980)].

Materials to perform all of these techniques are available from a variety of commercial sources such as Sigma Chemical Company in St. Louis, Mo.

Vaccine Components

*C. Perfringens* Alpha Toxoid: In particular embodiments it is advantageous for the animal vaccine to contain the minimum amount of the alpha toxoid required for protection against necrotic enteritis. That level was determined to be 2 Total Combining Power units (TCP) per dose under the particular conditions exemplified below. TCP units are set based upon international standards [Batty, *Toxin-Antitoxin Assay, Methods in Microbiology*, Chapter 8, Volume 5A (1971) ed. JR Norris and DW Ribbons] and the vaccines of the present invention can be readily blended to have the desired potency. Less than 2 TCP units may be used, even under these conditions, if the vaccine further comprises immune stimulants. In any case, it is preferable that the vaccine elicit 4 or more antitoxin units per mL of animal sera.

Quantifying Alpha Toxoid: It is generally desirable to quantify the alpha toxoid to ensure that optimal levels are included in the vaccine. One conventional method of quantifying toxoids employs the Total Combining Power (TCP) test. In this assay, a specific volume of the alpha toxoid supernatant is contacted with a known quantity of antitoxin units. After providing a suitable incubation period to allow the antitoxin and alpha toxoid to bind, e.g., 0.5-2 hours, a known quantity of the alpha toxin is added. The remaining free antitoxin then is given a suitable period to bind with the alpha toxin. The amount of free alpha toxin is then determined by adding to the solution a substrate for the phospholipase C activity of the alpha toxin. Suitable substrates include red blood cells (particularly sheep red blood cells) and lecithin. The alpha toxoid can then be quantified through a calculation based upon the amount of phospholipase C activity.

The greater the amount of alpha toxoid present in the assay solution, the greater the amount of phospholipase C activity measured in the assay. Alternatively, the determination may be made without measuring the phospholipase C activity, e.g., any competitive antibody binding analysis may be used, including incorporating a chromatography step, enzyme linked immunosorbant assay (ELISA), or competitive binding analysis by a Biacore instrument or the like.

Additional Antigens: Clostridial diseases often occur as mixed infections and therefore the addition of other clostridial toxoids may further reduce pathology and clinical signs. Non-limiting examples of other clostridial toxoids from organisms which are known to cause gastric enteritis, including those from *C. perfringens*, that may be added to a vaccine of the present invention to increase potency against mixed infections include: *C. perfringens* beta toxin, beta 2 toxin, theta toxin, epsilon toxin, enterotoxin, kappa toxin, lambda toxin and iota toxin; *C. sordellii* hemorrhagic toxin (HT) and lethal toxin (LT), *C. difficile* A and B toxins; *C. septicum* alpha toxin; and *C. novyi* alpha (A) and beta (B) toxins.

Antigens from other bacteria, viruses, fungi, or parasites may also be included in the vaccines of the present invention. Such antigens include other toxins or toxoids, bacteria and/or extracts from bacteria; fungi and/or extracts from fungi; viruses and/or viral proteins; and/or parasites or proteins from parasites. Appropriate viral, bacterial, and parasitic antigens from the sources provided herein are well known in the art.

Non-limiting examples of bacterial organisms are: *Escherichia coli, Camplobacter* spp., *Pasteurella* spp., *Staphylococcus* spp., *Streptococcus* spp., *Enterococcus* spp., *Chlamydia*, Erysipelas spp. *Pasteurella, Bordetella*, and *Ornithobacterium.*

Non-limiting examples of related toxins are: Gram negative bacteria lypopolysaccharide (LPS), which is known to enhance the immunological response of vaccines and thus improve the production of antitoxins to the alpha toxin of *C. perfringens* and mycotoxins.

Non-limiting examples of appropriate viruses are: Coronavirus, Rotavirus, Astrovirus, Enteroviruslike virus, Torovirus, Adenovirus, Reovirus, Birnavirus, Herpesvirus, Paramyxovirus, Picornavirus, Mareks Disease Virus, Hemorrhagic Enteritis Virus, and Newcastle Disease Virus.

Non-limiting examples of parasites are: Coccidia, the *Eimeria* species for example, and Cryptosporidia, [see, US 2004/0018215A1, the contents of which are hereby incorporated by reference in their entireties].

Adjuvants

Adjuvants are also useful for improving the immune response and/or increasing the stability of vaccine preparations. Adjuvants are typically described as non-specific stimulators of the immune system, but also can be useful for targeting specific arms of the immune system. One or more compounds which have this activity may be added to the vaccine. Therefore, particular vaccines of the present invention further comprise an adjuvant. Examples of chemical compounds that can be used as adjuvants include, but are not limited to aluminum compounds (e.g., aluminum hydroxide), metabolizable and non-metabolizable oils, mineral oils including mannide oleate derivatives in mineral oil solution (e.g., MONTANIDE ISA 70 from Seppic SA, France), and light mineral oils such as DRAKEOL 6VR, block polymers, ISCOM's (immune stimulating complexes), vitamins and minerals (including but not limited to: vitamin E, vitamin A, selenium, and vitamin B12) and CARBOPOL®.

Other suitable adjuvants, which sometimes have been referred to as immune stimulants, include, but are not limited to: cytokines, growth factors, chemokines, supernatants from cell cultures of lymphocytes, monocytes, cells from lymphoid organs, cell preparations and/or extracts from plants, bacteria or parasites (*Staphylococcus aureus* or lipopolysaccharide preparations) or mitogens.

Generally, an adjuvant is administered at the same time as an antigen of the present invention. However, adjuvants can also, or alternatively be administered within a two-week period prior to the vaccination, and/or for a period of time after vaccination, i.e., so long as the antigen, e.g., an alpha toxoid, persists in the tissues.

Preparation of Vaccines

Processes for making the vaccines of the present invention are also provided. In one embodiment, the vaccine comprises blending a safe and immunologically effective combination of an antigen of the present invention, e.g., an alpha toxoid supernatant of a single *C. perfringens* Type, and a pharmaceutically acceptable adjuvant. The amount of alpha toxoid can be quantified to contain at least 2 total combining power (TCP) units per dose of the vaccine. The alpha toxoid supernatant can be concentrated to minimize the dose size required to obtain at least 4.0 antitoxin units (A.U.) per mL of antisera from a vaccinated animal. The addition of other pharmaceutically acceptable immune modulation agents can reduce the TCP requirement to fall below 2 units per dose, so long as the vaccination still results in the requisite 4.0 A.U. of anti-alpha toxin antibody per mL of antisera from the vaccinated animal. In certain embodiments, the *C. perfringens* alpha toxoid is further purified from the alpha toxoid supernatants by such techniques as, but not limited to, concentration/ultrafiltration, chromatography and centrifugation.

Administration of Vaccines

Vaccines may be administered as a liquid, emulsion, dried powder and/or in a mist through any parenteral route, intravenously, intraperitoneally, intradermally, by scarification, subcutaneously, intramuscularly, or inoculated by a mucosal route, e.g., orally, intranasally, as an aerosol, by eye drop, by in ovo administration, or implanted as a freeze dried powder.

Animal Subjects

The term "animal subject" refers to an animal species capable of being infected by a pathogenic bacterium, and in a particular embodiment includes humans. Appropriate animal subjects also include those in the wild, livestock (e.g., raised for meat, milk, butter, eggs, fur, leather, feathers and/or wool), beasts of burden, research animals, companion animals, as well as those raised for/in zoos, wild habitats and/or circuses.

In a particular embodiment an animal subject of the invention is a "food producing" animal. For purposes of the present invention, the term "food-producing" animal shall be understood to include all animals bred for consumption (e.g., turkeys, broiler chickens) or for consumables (e.g., dairy cows, egg-laying hens, and the like) by humans and/or other animals. A non-limiting list of such animals include avians such as poultry, i.e., chickens, turkeys, geese, duck, ostriches, etc., bovines (e.g., cattle, dairy cows, buffalo), ovines (e.g., goats or sheep), porcines (e.g., swine, hogs or pigs), and equines (e.g., horses) etc.

In another embodiment, the animal subject is a companion animal. For purposes of the present invention, the term "companion" animal shall be understood to include house-cats (feline), dogs (canine), rabbit species, horses (equine), rodents (e.g., guinea pigs, squirrels, rats, mice, gerbils, and hamsters), primates (e.g., monkeys) and avians, such as pigeons, doves, parrots, parakeets, macaws, canaries, and the like.

Other animals are also contemplated to benefit from the inventive vaccines, including marsupials (such as kangaroos), reptiles (such as farmed turtles), game birds, swans, ratites, and other economically important domestic animals.

The following examples are intended for exemplification of the present invention only and should not be construed to limit the scope of the invention in any way.

EXAMPLES

Example 1

Efficacy of Vaccine in Broiler Hens Vaccinated by a Subcutaneous Route

Summary

Vaccinating broiler hens by a subcutaneous route using a vaccine comprising a single *C. perfringens* Type alpha toxoid (Type A) results in (i) an immunogenic response in the vaccinated broiler hens, (ii) significant anti-alpha toxoid antibody in the eggs of the vaccinated broiler hens, and (iii) passive protection of the subsequently born offspring of the vaccinated broiler hens.

Materials

*C. Perfringens* Type A alpha toxoid: *C. perfringens* Type A alpha toxoid is prepared as follows: *C. perfringens* Type A culture is grown under anaerobic conditions in a large scale fermenter (5000 L) at a temperature of 37° C.±2. During fermentation sodium hydroxide is added in order to maintain a pH of 7.8±2. Carbohydrate (dextrin) is also added during the fermentation (up to 1% w/v) to promote growth. The culture is allowed to grow for 3-6 hours. At the end of the growth period, formaldehyde solution is added to the fermenter to a final level not to exceed 0.5%. Cells are removed by centrifugation and the resulting supernatant is filtered with a depth filter having pore sizes in the range of 0.25-2.0 μm. The temperature is maintained at 5° C.±3° C. during this process. The inactivated culture supernatant is then diafiltered and concentrated 10-30 fold using ultrafiltration with filters not greater than 20,000 molecular weight cutoff. Concentrated supernatant is stored at 2-8° C. for future blending into vaccines. Prior to blending, the concentrated supernatant is assayed for potency by using the combining power test (TCP) described above. The potency of each batch of toxoid is assigned in TCP units per mL.

Vaccine: The supernatant comprising the inactivated *C. perfringens* type A alpha toxoid is blended as a water-in-oil emulsion containing 4 Combining Power Units (TCP) per mL. The emulsion is prepared with 70% oil phase and 30% aqueous phase.

The oil phase is prepared as follows:

| | |
|---|---|
| Mineral oil | 89.20% |
| Span 80 | 10.00% |
| Benzyl alcohol | 0.75% |
| Triethanolamine | 0.05% |

The aqueous phase is prepared as follows:

| | |
|---|---|
| C. perfringens type A toxo

TABLE 3-continued

NECROTIC ENTERITIS LESION SCORES IN
INDIVIDUAL PROGENY CHICKS FROM 52 WEEK-OLD HENS

| Non-vaccinated non-challenged controls | Non-vaccinated challenge controls | Vaccine with 2 TCP per dose |
|---|---|---|
| | 1 | |
| | | 0 |
| | 1 | |
| | | 0 |
| | 1 | |
| | | 0 |
| | 2 | |
| | | 0 |
| Mean = 0 | 1.7 | 0.6 |
| Median = 0 | 1.5 | 0.5 |

TABLE 4

NECROTIC ENTERITIS LESION SCORES IN
INDIVIDUAL PROGENY CHICKS FROM 65 WEEK-OLD HENS

| Non-vaccinated non-challenged controls | Non-vaccinated challenge controls | Vaccine with 2 TCP per dose |
|---|---|---|
| 0 | 4 | 0 |
| 0 | 0 | 0 |
| 0 | 0 | 0 |
| 0 | 2 | 2 |
| | 0 | 2 |
| | 0 | 0 |
| | 3 | 0 |
| | 3 | 3 |
| | 2 | 0 |
| | 0 | 2 |
| | 3 | 0 |
| | 2 | 0 |
| | 0 | 0 |
| | 0 | 0 |
| | 0 | |
| | 2 | |
| | 3 | |
| | 3 | |
| Mean = 0 | 1.5 | 0.6 |
| Median = 0 | 2.0 | 0.0 |

TABLE 5

MEDIAN SCORE IN PROGENY CHICKS FROM
HENS VACCINATED WITH A DOSE OF 2 TCP

| TREATMENT GROUPS | MEDIAN NECROTIC ENTERITIS LESION SCORE FROM PROGENY OF HENS | | |
|---|---|---|---|
| | 32 WEEKS OLD | 52 WEEKS OLD | 65 WEEKS OLD |
| Vaccinate group | 1 | 0.5 | 0 |
| Control group | 2 | 1.5 | 2 |

Antibody Titers

Sera: Blood samples are collected from hens at 33 and 78 weeks of age. Blood is allowed to clot for 2-4 hours at room temperature and then sera is obtained following centrifugation. Sera is stored at −10° C. or colder until tested for antibody titer. The antibody titer to *C. perfringens* alpha toxin is evaluated by a haemolysis inhibition assay using serial dilutions and sheep red blood cells as follows: Serial dilutions (two-fold) are made in a V-bottom microtiter plate for each sample tested. A known amount of alpha toxin is added to each well containing a dilution of the sample. The plates are then incubated for one hour at 36±2° C. to allow the antibodies obtained from the sera to complex with the alpha toxin. Following this incubation, a 0.5% solution of sheep red blood cells are added to the wells and the plates are incubated for three hours at 36° C.±2° C. to allow uncomplexed alpha toxin to lyse the red blood cells. The plates are then checked for the absence of haemolysis. The reciprocal of the highest dilution of the test sample that shows no haemolysis is considered the end point. The antibody titers are shown in Tables 6-8.

Egg Yolks: Egg yolks are processed to determine the antibody titer. Briefly, the yolk is separated and mixed with commercial extraction buffer (Promega EGGstract System□, Promega Catalog No. G1531 and G2610, Madison, Wis.). Following the extraction, an IgY pellet is obtained, which is then resuspended to the original volume of yolk with phosphate buffered saline. Egg yolk extract is pooled from at least 5 eggs and tested for antibody titer using a haemolysis inhibition (HI) assay as described for the sera above. The yolks from eggs collected from layers at 40, 52, and 65 weeks of age are evaluated for antibody titer in this manner. The antibody titers for the egg yolks are shown in Table 9.

TABLE 6

| INDIVIDUAL HEN SERUM ANTIBODY TITER TO *C. PERFRINGENS* TYPE A ALPHA TOXIN AT 33 WEEKS OF AGE | |
|---|---|
| Vaccinated hens (2 TCP/Dose) | Control hens* |
| 1024 | 1 |
| 8192 | 2 |
| 256 | 1 |
| 1024 | 2 |
| 1024 | 2 |
| 256 | 2 |
| 256 | 2 |
| 1024 | 2 |
| 512 | 1 |
| 64 | 1 |
| Geomean = 588 | Geomean ≤2 |

*Values <2 were considered as 1 for the purpose of calculating the geometric mean

TABLE 7

| INDIVIDUAL HEN SERUM ANTIBODY TITER TO *C. PERFRINGENS* TYPE A ALPHA TOXIN AT 78 WEEKS OF AGE | |
|---|---|
| Vaccinated hens (2 TCP/Dose) | Control hens* |
| 512 | 2 |
| 32 | 2 |
| 128 | 2 |
| 512 | 2 |
| 128 | 1 |
| 16 | 1 |
| 1024 | 1 |
| 512 | 2 |
| 8192 | 2 |
| 128 | 4 |
| 64 | 2 |
| 512 | 8 |
| 64 | 16 |
| 1024 | |
| 256 | |
| 128 | |
| Geomean = 235 | Geomean = 2 |

*Values < 2 were considered as 1 for the purpose of calculating the geometric mean

TABLE 8

GEOMETRIC MEAN HAEMOLYSIS INHIBITION TITER
IN SERA OF HENS AT VARIOUS TIME POINTS

| TREATMENT GROUPS | TITER IN SERUM (AGE AT SAMPLE COLLECTION) | |
| --- | --- | --- |
| | 33 WEEKS | 78 WEEKS |
| VACCINATE GROUP (2 TCP/DOSE) | 588 | 235 |
| CONTROL GROUP | ≤2 | 2 |

TABLE 9

HAEMOLYSIS INHIBITION TITER IN EGG YOLK FROM
HENS COLLECTED AT VARIOUS TIME POINTS

| TREATMENT GROUPS | TITER IN EGG YOLK (AGE AT EGG COLLECTION) | | |
| --- | --- | --- | --- |
| | 40 WEEKS | 52 WEEKS | 65 WEEKS |
| VACCINATE GROUP | 515 | 2048 | 64 |
| CONTROL GROUP | ≤2 | 2 | ≤2 |

Example 2

Efficacy of Vaccine in Broiler Hens Vaccinated by an Intramuscular Route

Summary

Vaccination of broiler hens by an intramuscular route using a vaccine comprising a single *C. perfringens* Type alpha toxoid (Type A), also results in (i) an immunogenic response in the vaccinated broiler hens, (ii) significant anti-alpha toxoid antibody in the eggs of the vaccinated broiler hens, and (iii) passive protection for the subsequently born offspring of the vaccinated broiler hens.

Passive Immunity

A total of 14 broiler pullets are intramuscularly vaccinated with two doses of a 0.5 mL of the vaccine of Example 1 above, containing 2 TCP. An additional group of 40 pullets are used as controls. Three roosters are commingled with each group of pullets, as described above. The first dose of vaccine is administered at 10 weeks of age and the second dose is administered at 23 weeks of age. The eggs are collected from the hens at 32 weeks of age and hatched to determine passive protection in the progeny chicks following an experimental *C. perfringens* challenge.

Table 10 shows the incidence of necrotic enteritis and the median score for its corresponding lesions as determined by the Rating Scale of Example 1 above, for the progeny chicks of vaccinated and control hens. Table 11 shows that median score for the necrotic enteritis lesions for the individual progeny chicks. Table 12 lists the antibody titers against *C. perfringens* Type A alpha toxin of the individual progeny chicks, whereas, the antibody titers for the egg yolks from eggs collected from the vaccinated and control hens at 32 weeks of age are provided in Table 13.

TABLE 10

| INCIDENCE OF DISEASE AND NECROTIC ENTERITIS LESION | | | | |
|---|---|---|---|---|
| TREATMENT GROUPS | Number of birds | % Incidence | Median Score | Mean Score |
| VACCINATE GROUP | 8 | 0 (0/8) | 0 | 0 |
| CONTROL GROUP | 29 | 76 (22/29) | 2 | 1.7 |

TABLE 11

| NECROTIC ENTERITIS LESION SCORES IN INDIVIDUAL PROGENY CHICKS FROM 32 WEEK-OLD HENS | | |
|---|---|---|
| Non-vaccinated non-challenged controls | Non-vaccinated challenge controls | Vaccine with 2 TCP per dose |
| 0 | 1 | 0 |
| 0 | 2 | 0 |
| 0 | 1 | 0 |
| 0 | 0 | 0 |
| 0 | 0 | 0 |
| 0 | 1 | 0 |
| | 3 | 0 |
| | 0 | 0 |
| | 1 | |
| | 0 | |
| | 2 | |
| | 2 | |
| | 1 | |
| | 3 | |
| | 3 | |
| | 3 | |
| | 2 | |
| | 2 | |
| | 3 | |
| | 1 | |
| | 3 | |
| | 0 | |
| | 2 | |
| | 0 | |
| | 0 | |
| | 3 | |
| | 2 | |
| | 4 | |
| | 4 | |
| Mean = 0.0 | 1.7 | 0.0 |
| Median = 0.0 | 2.0 | 0.0 |

TABLE 12

| SERUM ANTIBODY TITER OF INDIVIDUAL HENS AT 35 WEEKS OF AGE[2] | |
|---|---|
| VACCINATED HENS (2 TCP/Dose) | CONTROL HENS[3] |
| 128 | 1 |
| 512 | 1 |
| 65536 | 1 |
| 4096 | 1 |
| 1024 | 1 |
| 512 | 1 |
| 2048 | 1 |
| 1024 | 1 |
| 512 | 2 |
| 256 | 1 |
| 1024 | 1 |
| 128 | 1 |
| 256 | 1 |
| 256 | 1 |
| 1024 | 1 |

TABLE 12-continued

SERUM ANTIBODY TITER OF INDIVIDUAL HENS AT 35 WEEKS OF AGE[2]

| VACCINATED HENS (2 TCP/Dose) | CONTROL HENS[3] |
|---|---|
| 1024 | 2 |
| 64 | 32 |
| 681 | 2 |
|  | 2 |
|  | 1 |
|  | 2 |
|  | 1 |
|  | 1 |
|  | 2 |
|  | 2 |
|  | 2 |
|  | 1 |
|  | 2 |
|  | 32 |
|  | 1 |
|  | 2 |
|  | 1 |
|  | 1 |
|  | 2 |
|  | 1 |
|  | 1 |
|  | 1 |
| Geomean = 681 | ≤2 |

[2]Antibodies to *C. perfringens* Type A Alpha Toxin as Measured by Haemolysis Inhibition Assay described in Example 1 above.
[3]Values < 2 were considered as 1 for the purpose of calculating the geometric mean.

TABLE 13

| ANTIBODY TITER IN EGG YOLK COLLECTED FROM HENS AT 32 WEEKS OF AGE | |
|---|---|
| TREATMENT GROUPS | HAEMOLYSIS INHIBITION TITER |
| VACCINATE GROUP | 512 |
| CONTROLS GROUP | <2 |

Example 3

Serology in SPF White Leghorn Pullets Vaccinated by a Subcutaneous Route

Antibody Titers

Antibody titers are evaluated in SPF white leghorn pullets that are vaccinated subcutaneously with the vaccine of Example 1 above, containing 1, 2, or 3 TCP. The pullets are vaccinated at 15 weeks of age with 0.5 mL of the vaccine and a booster dose is administered 4 weeks following the initial vaccination. Blood samples are collected 6 weeks following the booster vaccination. Serum from each individual bird is evaluated for antibody titer by the haemolysis inhibition assay as described above in Example 1.

TABLE 14

INDIVIDUAL PULLET SERUM ANTIBODY TITER TO *C. PERFRINGENS* TYPE A ALPHA TOXIN

| 1 TCP/DOSE | | 2 TCP/DOSE | | 3 TCP/DOSE | | CONTROLS | |
|---|---|---|---|---|---|---|---|
| Bird Id | Titer | Bird Id | Titer | Bird Id | Titer | Bird Id | Titer* |
| 923 | 4096 | 932 | 1024 | 922 | 1024 | 921 | 4 |
| 924 | 1024 | 938 | 8192 | 927 | 64 | 928 | <2 |

TABLE 14-continued

INDIVIDUAL PULLET SERUM ANTIBODY TITER TO *C. PERFRINGENS* TYPE A ALPHA TOXIN

| 1 TCP/DOSE | | 2 TCP/DOSE | | 3 TCP/DOSE | | CONTROLS | |
|---|---|---|---|---|---|---|---|
| Bird Id | Titer | Bird Id | Titer | Bird Id | Titer | Bird Id | Titer* |
| 925 | 4 | 940 | 512 | 931 | 2048 | 929 | 2 |
| 926 | 2048 | 942 | 1024 | 935 | 4096 | 933 | 2 |
| 930 | 512 | 943 | 2048 | 945 | 1024 | 937 | 2 |
| 941 | 1024 | 948 | 2048 | 947 | 2048 | 946 | 2 |
| 953 | 32 | 949 | 2048 | 952 | 1024 | 957 | 2 |
| 954 | 2 | 950 | 2048 | 956 | 128 | 966 | <2 |
| 955 | 32 | 951 | 512 | 959 | 512 | | |
| 962 | 512 | 958 | 512 | 960 | 64 | | |
| 965 | 4096 | 961 | 512 | 963 | 2048 | | |
| 967 | 512 | 964 | 2048 | 968 | 2048 | | |
| Geomean | 242 | | 1290 | | 724 | | ≤2 |

*Titers of <2 are considered as 1 for determining geometric mean titer

The antibody titer in the eggs collected at 25 week of age from the white leghorn layers are evaluated for haemolysis inhibition titer. The results are tabulated in Table 15.

TABLE 15

| POOLED EGG YOLK ANTIBODY TITER TO *C. PERFRINGENS* TYPE A ALPHA TOXIN | | |
|---|---|---|
| GROUP | VACCINE | ANTIBODY TITER |
| 1 | 1 TCP | 512 |
| 2 | 2 TCP | 512 |
| 3 | 3 TCP | 512 |
| 4 | Controls | <2 |

Determination of Toxin Neutralization Titer (TNT) in Pooled Sera of White Leghorn Hens Antitoxin titer to *C. perfringens* Type A alpha toxin in the pooled serum of the hens is evaluated using mice. The pooled sera are tested for antitoxin titer using a method as described in Code of Federal Regulations, Animal and Plant Health Inspection Service, Department of Agriculture. The methods used to measure the antitoxin was similar to the current 9 CFR §113.111 (c), except that alpha toxin and antitoxin reagents are used instead of beta toxin and antitoxin. The following test reagents are used to determine the antitoxin titer:

1) *C. perfringens* Type A alpha antitoxin: IRP 426 (obtained from Center for Veterinary Biologics, USDA).

2) *C. perfringens* Type A alpha toxin IRP 446 (obtained from Center for Veterinary Biologics, USDA).

Briefly, diluted standard antitoxin or sera are combined with a known amount of standard alpha toxin. The presence of un-neutralized toxin is then detected by injection of the mixture into mice. Comparison to the effects of known amounts of standard alpha antitoxin on toxin activity are then evaluated by determining the dilution of standard or test sera that protects the mice from death in a bioassay. The antitoxin titer in the pooled sera of white leghorn pullets are as shown in Table 16 below.

TABLE 16

TOXIN NEUTRALIZATION TITER (TNT)
IN VACCINATED AND CONTROL PULLETS

| GROUP | VACCINE | ANTITOXIN TITER IN SERUM | |
|---|---|---|---|
| | | Pre-vaccination | Post-vaccination |
| 1 | 1 TCP | <1 | ≥2 and <4 |
| 2 | 2 TCP | <1 | ≥4 |
| 3 | 3 TCP | <1 | ≥4 |
| 4 | Controls | <1 | <1 |

Example 4

Serology in SPF White Leghorn Pullets Vaccinated by an Intramuscular Route

Antibody Titers

Antibody titers in SPF white leghorn pullets that are vaccinated twice intramuscularly with vaccine of Example 1 above, containing 1, 2, or 3 TCP are evaluated. The pullets are vaccinated at ten weeks of age with 0.5 mL of the vaccine and a booster dose is given four weeks following initial vaccination. Blood samples are collected seven weeks following booster vaccination. The individual pullet sera is evaluated for antibody titer by haemolysis inhibition assay as described in Example 1 above, and is tabulated in Tables 17 and 18 below.

TABLE 17

INDIVIDUAL PULLET SERUM ANTIBODY TITER
TO C. PERFRINGENS TYPE A ALPHA TOXIN

| 1 TCP | | 2 TCP | | 3 TCP | | Controls | |
|---|---|---|---|---|---|---|---|
| Bird Id | Titer | Bird Id | Titer | Bird Id | Titer | Bird Id | *Titer |
| 951 | 256 | 631 | 1024 | 646 | 4096 | 661 | <2 |
| 952 | 128 | 632 | 2048 | 647 | 4096 | 662 | <2 |
| 953 | 1024 | 633 | 2048 | 648 | 2048 | 663 | 8 |
| 954 | 128 | 634 | 256 | 649 | 2048 | 664 | <2 |
| 955 | 2048 | 635 | 128 | 650 | 4096 | 665 | 8 |
| 956 | 512 | 636 | 2048 | 651 | 2048 | 666 | 4 |
| 957 | 1024 | 637 | 512 | 652 | 2048 | 667 | <2 |
| 958 | 256 | 638 | 2048 | 653 | 1024 | 668 | <2 |
| 960 | 512 | 639 | 1024 | 654 | 4096 | 669 | <2 |
| 961 | 2048 | 640 | 2048 | 655 | 4096 | 670 | <2 |
| 962 | 1024 | 641 | 2048 | 656 | 4096 | 671 | <2 |
| 964 | 1024 | 642 | 1024 | 657 | 4096 | 672 | <2 |
| 965 | 256 | 643 | 1024 | 658 | 1024 | 673 | 16 |
| | | 644 | 512 | 660 | 1024 | 674 | 16 |
| | | 645 | 2048 | 966 | 4096 | 675 | 16 |
| Geomean | 540 | | 1024 | | 2580 | | 3 |

*Titers of <2 are considered as 1 for determining geometric mean titer

Toxin neutralization titer (TNT) in pooled sera of hens is evaluated using the procedure as described in Example 3 above, and the results are provided in Table 18 below.

TABLE 18

TOXIN NEUTRALIZATION TITER (TNT)
IN VACCINATED AND CONTROL PULLETS

| GROUP | VACCINE | ANTITOXIN TITER IN SERUM | |
|---|---|---|---|
| | | Pre-vaccination | Post-vaccination |
| 1 | 1 TCP | <1 | ≥4 |
| 2 | 2 TCP | <1 | ≥4 |
| 3 | 3 TCP | <1 | ≥4 |
| 4 | Controls | <1 | <1 |

The antibody titer in the eggs collected at 25 week of age from these white leghorn layers are evaluated for haemolysis inhibition titer as described in Example 1 above. The results are summarized below in Table 19.

TABLE 19

POOLED EGG YOLK ANTIBODY TITER TO
C. PERFRINGENS TYPE A ALPHA TOXIN

| GROUP | VACCINE | ANTIBODY TITER |
|---|---|---|
| 1 | 1 TCP | 512 |
| 2 | 2 TCP | 256 |
| 3 | 3 TCP | 512 |
| 4 | Controls | <2 |

Example 5

Comparison of a Mutivalent and a Monovalent C. Perfringens Alpha Toxoid Vaccine in Porcine

Summary

Methods are described for providing passive protection in neonatal pigs by vaccinating the pregnant sows/gilts with the *C. perfringens* type A alpha toxoid vaccines of the present invention. The results show an antibody response in sows that can be transferred to piglets through colostrum.

Materials

*C. Perfringens* Type A Alpha Toxoid: *C. perfringens* Type A alpha toxoid was prepared as described in Example 1 above.

Vaccine: A vaccine of the present invention can be blended with inactivated *C. perfringens* type A alpha toxoid containing >2 Total Combining Power Units. The vaccine can be blended with any adjuvant disclosed herein, including oil-in-water emulsion containing mineral oils, vegetable oils (peanut oil, soybean oil), squalene, squalane and other metabolizable oils. Other adjuvants such as Seponin, CARBOPOL®, and aluminum containing adjuvants (aluminum hydroxide, aluminum phosphate) also can be used in vaccine preparation. The vaccine can further contain other antigens including *E. coli* (K88, K99, 987P, Type 1), toxoids from *C. perfringens*, and/or toxoids from other pathogenic bacteria including *Clostridium difficile*, rotavirus, and/or Cryptosporedia.

Administration

The vaccines are administered to pregnant gilts/sows prior to farrowing by either intramuscular or subcutaneous route in order to provide passive protection in neonatal pigs though the ingestion of colostrum.

Results

The study is conducted in 32 week-old pigs comparing three vaccines:

Vaccine #1: blended with an aluminum hydroxide adjuvant containing 4 TCP of *C. perfringens* Type A alpha toxoid in a 2 mL dose.

Vaccine #2: blended with 4 TCP of *C. perfringens* type A alpha toxoid, *E. coli* K88, *E. coli* K99, *E. coli* 987P, *E. coli* Type 1 and *C. perfringens* type C beta toxoid in a 2 mL dose.

Vaccine #3: prepared as a placebo vaccine containing no *C. perfringens* type A alpha toxoid, but containing *E. coli* K88, *E. coli* K99, *E. coli* 987P, *E. coli* Type 1 and *C. perfringens* type C beta toxoid in a 2 mL dose.

One group of ten pigs is vaccinated intramuscularly with 2 mL of Vaccine #1. A second group of ten pigs is vaccinated intramuscularly with 2 mL of Vaccine #2. The third group of seven pigs is vaccinated with 2 mL of Vaccine #3. A booster dose of 2 mL is given 20 days following the initial vaccinations. The sera samples are collected at the time of initial vaccination (Day 0), 20 days after the booster vaccination (Day 40) and 41 days after booster vaccination (Day 61). The sera samples are then evaluated for antibody titer to alpha toxin by the haemolysis inhibition assay described in Example 1 above. The results for the three vaccines are individually shown in Tables 20-22, respectively.

TABLE 20

MONOVALENT *C. PERFRINGENS* TYPE A ALPHA TOXOID VACCINE
Haemolysis Inhibition Titer

| Pig # | Day 0 (Pre-vac) | Day 40 | Day 61 |
|---|---|---|---|
| 10268 | 32 | 256 | 256 |
| 10277 | 2 | 8 | 8 |
| 10278 | 16 | 32 | 32 |
| 10295 | 16 | 64 | 128 |
| 10307 | 16 | 64 | 128 |
| 10312 | 8 | 64 | 64 |
| 10316 | 2 | 16 | 16 |
| 10317 | — | 64 | 64 |
| 10324 | 64 | 128 | 256 |
| 10331 | 16 | 32 | 32 |
| Geomean | 12 | 49 | 60 |

TABLE 21

*C. PERFRINGENS* TYPE A ALPHA TOXOID COMBO VACCINE WITH *E. COLI*-*C. PERFRINGENS* TYPE C BETA TOXOID
Haemolysis Inhibition Titer

| Pig # | Day 0 (Pre-vac) | Day 40 | Day 61 |
|---|---|---|---|
| 10264 | 16 | 64 | 64 |
| 10266 | 32 | 128 | 128 |
| 10269 | 2 | 32 | 32 |
| 10276 | 2 | 256 | 256 |
| 10280 | 8 | 32 | 32 |
| 10282 | 4 | 32 | 32 |
| 10287 | 16 | 64 | 64 |
| 10290 | 16 | 256 | 256 |
| 10321 | 16 | 128 | 64 |
| 10330 | 4 | 64 | 64 |
| Geomean | 8 | 79 | 74 |

TABLE 22

*E. COLI* - *C. PREFRINGENS* TYPE C BETA TOXOID
Haemolysis Inhibition Titer

| Pig # Group 3 | Day 0 (Pre-vac) Day 0 | Day 40 Day 40 | Day 61 Day 61 |
|---|---|---|---|
| 10272 | 4 | 32 | 32 |
| 10292 | 16 | 32 | 32 |
| 10303 | 2 | 16 | 16 |
| 10305 | 2 | 32 | 32 |
| 10313 | 8 | 8 | 8 |
| 10318 | 4 | 16 | 16 |
| 10319 | 4 | 64 | 64 |
| Geomean | 4 | 24 | 24 |

Example 6

Determination of Toxin Neutralization Titer (TNT) in Pooled Sera of Vaccinated Sows Four pregnant sows are evenly divided into two treatment groups. One group is vaccinated by intramuscular route with 2.0 mL of vaccine containing 4 TCP in a 2 mL dose of Vaccine #1 of Example 5 above. The other group is the controls who are not vaccinated. The sows are vaccinated at approximately 6-7 weeks prior to farrowing, and a booster dose is given three weeks later. Blood samples are collected before vaccination, and just prior to farrowing. Table 23 shows the evaluation of the sera samples for antitoxin titer to alpha toxin using a toxin neutralization test (TNT) as described in Example 3 above.

TABLE 23

TNT TITER

| Treatment Group | Sow Number | Pre-vaccination (TNT) | Post-Booster vaccination (TNT) |
|---|---|---|---|
| Vaccinate | 10614 | <1 | >4 < 8 |
| Vaccinate | 10616 | <1 | >4 < 8 |
| Control | 10615 | <2 | <2 |
| Control | 10617 | <1 | <2 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description. Various publications are cited herein, the disclosures of which are hereby incorporated by reference in their entireties.

What is claimed:

1. A vaccine against *Clostridium perfringens* (*C. perfringens*) comprising a *C. perfringens* Type A alpha toxoid supernatant that was concentrated by ultrafiltration and has 2 or more Total Combining Power (TCP);
    wherein the *C. perfringens* Type A alpha toxoid supernatant comprises a Type A alpha toxoid antigen; with the proviso that only a single *C. perfringens* Type alpha toxoid antigen is present in said vaccine; and wherein said vaccine is both safe and immunologically effective against a clostridial disease.

2. The vaccine of claim 1, wherein the antigen is in a cell-free preparation.

3. The vaccine of claim 1, wherein the antigen is a recombinant polypeptide.

4. The vaccine of claim 1, wherein the vaccine is for administration to a chicken and wherein one to two doses of 0.25 - 0.6 mL per dose of the vaccine is sufficient to induce at least four antitoxin units (A.U.) of anti-alpha toxin antibody per mL of antisera of a chicken vaccinated with the vaccine.

5. The vaccine of claim 1, further comprising an adjuvant.

6. The vaccine of claim 5, wherein a water-in-oil emulsion comprises the antigen and adjuvant.

7. The vaccine of claim 6, wherein the water-in-oil emulsion was prepared with a 70% oil phase and a 30% aqueous phase.

8. The vaccine of claim 1, which is a multivalent vaccine further comprising one or more of the following toxins: *C. perfringens* beta toxin, *C. perfringens* beta 2 toxin, *C. perfringens* enterotoxin, *C. perfringens* epsilon toxin, *C. perfringens* iota toxin, *C. perfringens* kappa toxin, *C. perfringens* lambda toxin, *C. perfringens* theta toxin, *C. sordellii* hemorrhagic toxin, *C. sordellii* lethal toxin, *C. difficile* A toxin, *C. difficile* B toxin, *C. septicum* alpha toxin, *C. novyi* alpha toxin, and *C. novyi* beta toxin.

9. The vaccine of claim 8, wherein the multivalent vaccine further comprises one or more viral antigens, one or more bacterial antigens, and one or more parasitic antigens;

wherein the one or more viral antigens is from one or more of the following sources: infectious bursal disease virus, infectious bronchitis virus, reovirus, and Newcastle disease virus;

wherein the one or more bacterial antigens is from one or more of the following sources: *E. coli, Salmonella*, and *Campylobacter*, and wherein the one or more parasite antigens is from *Eimeria.*

10. The vaccine of claim 1, which is a multivalent vaccine that further comprises one or more additional antigens;

wherein the additional antigen is from one or more of the following sources: infectious bursal disease virus, infectious bronchitis virus, reovirus, Newcastle disease virus, *E. coli, Salmonella, Campylobacter*, and *Eimeria.*

11. A method of providing passive immunity against a clostridial disease to the progeny of a female avian, said method comprising administering the vaccine of claim 1 to the female avian prior to her laying of the eggs that comprise the progeny; wherein the progeny are provided passive immunity.

12. The method of claim 11 wherein the avian is a chicken or a turkey.

13. The method of claim 11 wherein the clostridial disease is a clostridial enteric disease.

14. The method of claim 13 wherein the clostridial enteric disease is necrotic enteritis.

15. The method of claim 11 wherein the clostridial disease is selected from the group consisting of cholangiohepatitis, gangrenous dermatitis, and cellulitis.

16. A vaccine against *Clostridium perfringens* (*C. perfringens*) for a chicken comprising a C. perfringens Type A alpha toxoid supernatant that was concentrated by ultrafiltration and has 2 or more Total Combining Power (TCP);

wherein the *C. perfringens* Type A alpha toxoid supernatant comprises a Type A alpha toxoid antigen;

wherein a water-in-oil emulsion comprises the alpha toxoid antigen;

wherein one to two doses of 0.25-0.6 mL per dose of the vaccine is sufficient to induce at least four antitoxin units (A.U.) of anti-alpha toxin antibody per mL of antisera of a chicken vaccinated with the vaccine; and wherein said vaccine is both safe and immunologically effective against a clostridial disease; with the proviso that only a single *C. perfringens* Type alpha toxoid antigen is present in said vaccine.

17. The vaccine of claim 16 wherein the water-in-oil emulsion was prepared with a 70% oil phase and a 30% aqueous phase.

18. The vaccine of claim 16 wherein the clostridial disease is necrotic enteritis.

* * * * *